(12) United States Patent
Horton et al.

(10) Patent No.: US 8,628,495 B2
(45) Date of Patent: Jan. 14, 2014

(54) POWER INJECTOR SYRINGE ASSEMBLY

(75) Inventors: Duane L. Horton, St. Louis, MO (US); Felicia M. La Valle, Union, MO (US); Kevin R. Martz, St. Louis, MO (US)

(73) Assignee: Mallinckrodt LLC, Hazelwood, MI (US)

( * ) Notice: Subject to any disclaimer, the term of this patent is extended or adjusted under 35 U.S.C. 154(b) by 129 days.

(21) Appl. No.: 13/139,535

(22) PCT Filed: Aug. 11, 2010

(86) PCT No.: PCT/US2010/045101
§ 371 (c)(1),
(2), (4) Date: Jun. 14, 2011

(87) PCT Pub. No.: WO2011/019777
PCT Pub. Date: Feb. 17, 2011

(65) Prior Publication Data
US 2011/0251485 A1    Oct. 13, 2011

Related U.S. Application Data

(60) Provisional application No. 61/233,629, filed on Aug. 13, 2009.

(51) Int. Cl.
*A61M 1/00* (2006.01)
*A61M 5/00* (2006.01)

(52) U.S. Cl.
USPC ........... 604/151; 604/152; 604/154; 604/228; 604/232; 604/233; 600/432

(58) Field of Classification Search
USPC ......... 604/121, 135, 141, 151–152, 154–155, 604/228, 218, 232–233, 131
See application file for complete search history.

(56) References Cited

U.S. PATENT DOCUMENTS

| | | | |
|---|---|---|---|
| 2,734,504 A | | 2/1956 | Crescas et al. |
| 3,623,474 A | * | 11/1971 | Heilman et al. ............... 600/432 |
| 4,540,405 A | | 9/1985 | Miller et al. |
| 4,911,695 A | | 3/1990 | Lindner |
| 4,929,238 A | | 5/1990 | Baum |
| 5,007,904 A | | 4/1991 | Densmore et al. |
| D320,276 S | | 9/1991 | Baum |
| D321,053 S | | 10/1991 | Baum |
| 5,300,031 A | * | 4/1994 | Neer et al. ..................... 604/154 |
| 5,360,409 A | | 11/1994 | Boyd, III et al. |
| 5,520,653 A | | 5/1996 | Reilly et al. |
| 5,535,746 A | | 7/1996 | Hoover et al. |
| 5,947,929 A | | 9/1999 | Trull |
| 6,080,136 A | * | 6/2000 | Trull et al. ..................... 604/218 |

(Continued)

FOREIGN PATENT DOCUMENTS

| | | |
|---|---|---|
| EP | 0987040 A1 | 3/2000 |
| EP | 0987040 B1 | 9/2005 |

(Continued)

*Primary Examiner* — Quynh-Nhu H Vu

(57) ABSTRACT

A power injector syringe assembly (110) is disclosed. The power injector syringe assembly (110) includes a power injector syringe (112) and coupling (130) that are permanently joined. The coupling (130) includes a wedge-shaped mounting flange (144) to facilitate installation of the assembly (110) on a syringe mount (200) of a power injector. The coupling (130) also includes at least one coupling member (150) to facilitate removal of the assembly (110) from the syringe mount (200).

25 Claims, 20 Drawing Sheets

(56) References Cited

U.S. PATENT DOCUMENTS

| | | |
|---|---|---|
| 6,336,913 B1 | 1/2002 | Spohn et al. |
| 6,652,489 B2 | 11/2003 | Cowan et al. |
| 6,676,634 B1 | 1/2004 | Spohn et al. |
| 6,716,195 B2 | 4/2004 | Nolan, Jr. et al. |
| 6,726,657 B1 | 4/2004 | Dedig et al. |
| 6,743,205 B2 | 6/2004 | Nolan, Jr. et al. |
| 6,821,013 B2* | 11/2004 | Reilly et al. ............ 366/162.3 |
| 7,018,363 B2 | 3/2006 | Cowan et al. |
| 7,029,458 B2 | 4/2006 | Spohn et al. |
| 7,029,459 B2 | 4/2006 | Reilly |
| 7,192,417 B2 | 3/2007 | Thompson et al. |
| 7,273,477 B2 | 9/2007 | Spohn et al. |
| 7,497,843 B1 | 3/2009 | Castillo et al. |
| 2001/0047153 A1 | 11/2001 | Trocki et al. |
| 2002/0107481 A1 | 8/2002 | Reilly et al. |
| 2002/0177811 A1* | 11/2002 | Reilly et al. ............ 604/152 |
| 2003/0040719 A1* | 2/2003 | Spohn et al. ............ 604/228 |
| 2003/0120212 A1 | 6/2003 | Dedig et al. |
| 2004/0116893 A1* | 6/2004 | Spohn et al. ............ 604/500 |
| 2004/0122370 A1* | 6/2004 | Joyce et al. ............ 604/152 |
| 2005/0113754 A1 | 5/2005 | Cowan |
| 2007/0052409 A1* | 3/2007 | Cude ............ 324/120 |
| 2007/0088270 A1 | 4/2007 | Cude |
| 2007/0163079 A1 | 7/2007 | Cude |
| 2007/0233002 A1 | 10/2007 | Cude |
| 2008/0125714 A1 | 5/2008 | Cude |
| 2008/0292738 A1 | 11/2008 | Cude |
| 2008/0302697 A1 | 12/2008 | Cude |
| 2009/0043257 A1 | 2/2009 | Cude |
| 2011/0009836 A1* | 1/2011 | Chebli et al. ............ 604/298 |

FOREIGN PATENT DOCUMENTS

| | | |
|---|---|---|
| EP | 1351730 B1 | 6/2006 |
| GB | 662352 A | 11/1951 |
| WO | 9221392 A1 | 12/1992 |
| WO | 9709077 A1 | 3/1997 |
| WO | 9736635 A1 | 10/1997 |
| WO | 0108727 A1 | 2/2001 |
| WO | 02056945 A2 | 7/2002 |
| WO | 02056947 A1 | 7/2002 |
| WO | 03053554 A1 | 7/2003 |
| WO | 03101527 A1 | 12/2003 |
| WO | 2008127588 A1 | 10/2008 |
| WO | 2009039050 A1 | 3/2009 |

* cited by examiner

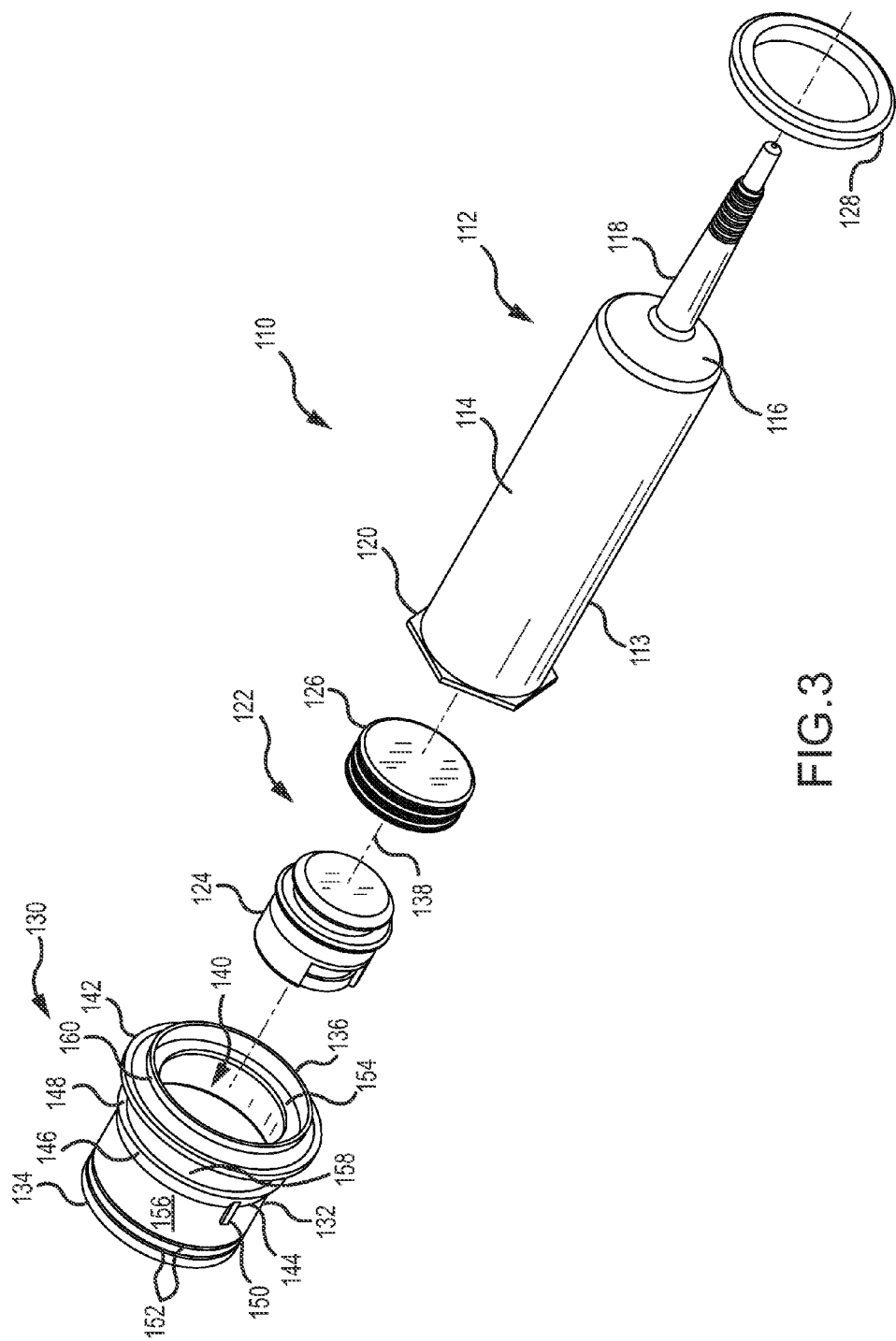

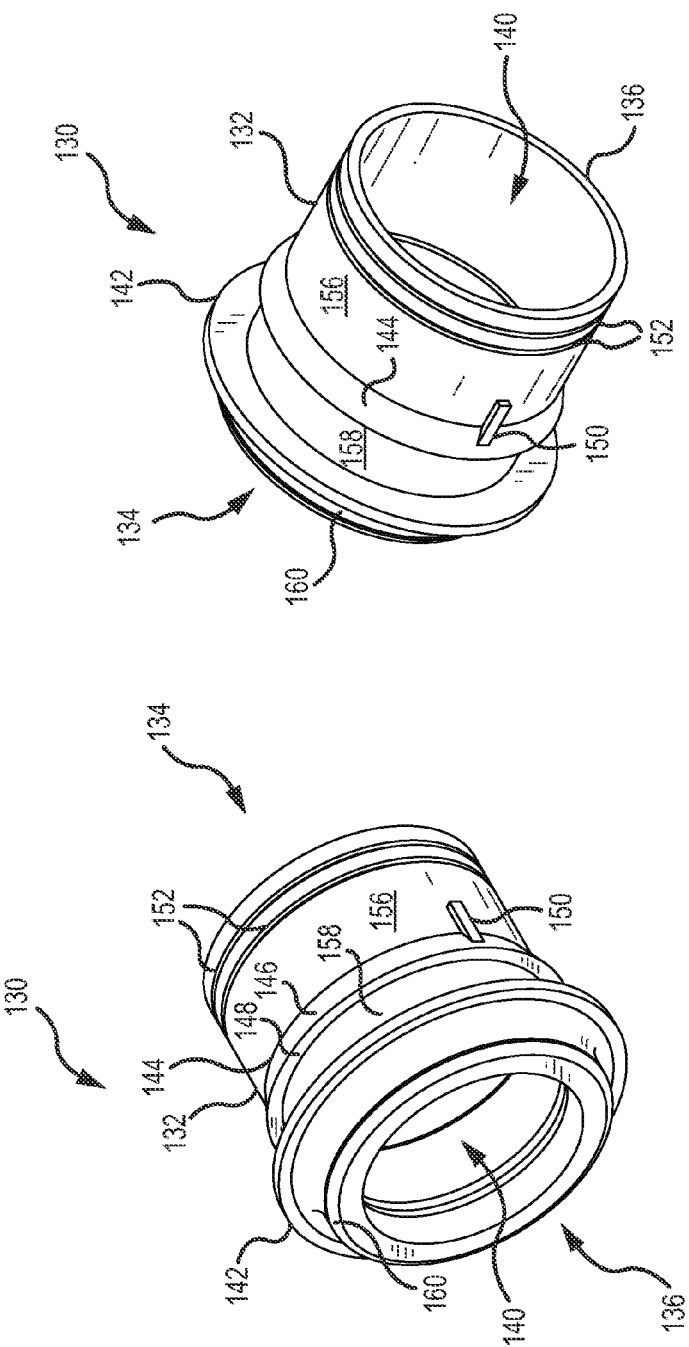

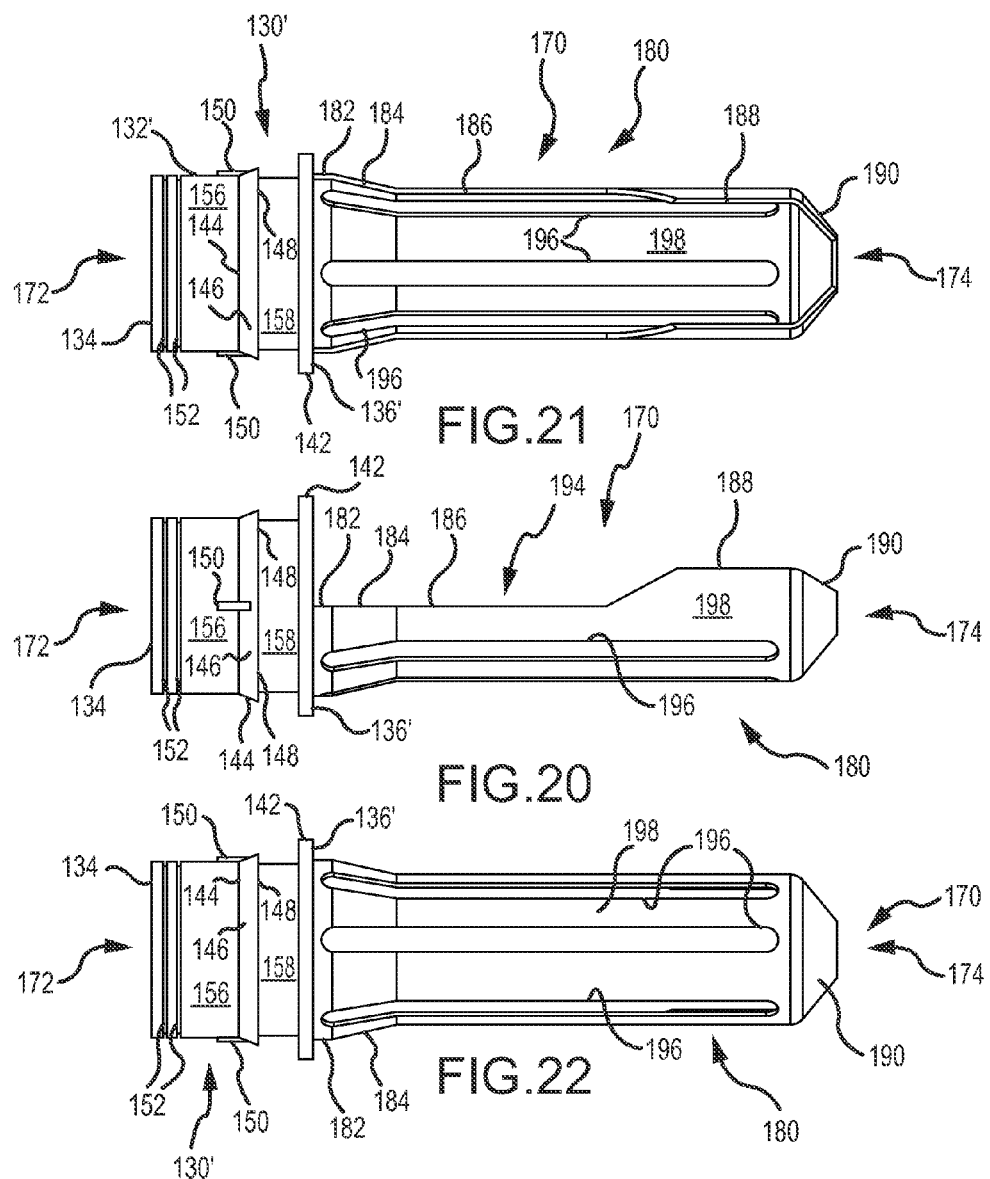

POWER INJECTOR SYRINGE ASSEMBLY

CROSS-REFERENCE TO RELATED APPLICATIONS

This patent application is a U.S. National Stage of PCT/US2010/045101, filed 11 Aug. 2010, which claims priority to and is a non-provisional application of U.S. Provisional Patent Application Serial No. 61/233,629 entitled "POWER INJECTOR SYRINGE ASSEMBLY" filed on 13 Aug. 2009. Priority is claimed to each patent application set forth in this Cross-Reference to Related Applications section.

FIELD OF THE INVENTION

The present invention generally relates to power injectors and, more particularly, to structures that accommodate installing syringes on power injectors.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

SUMMARY

A first aspect of the present invention is embodied by a power injector syringe assembly that includes a power injector syringe, a coupling, and a retention ring. The power injector syringe includes a syringe barrel, a syringe flange, and a plunger that is movable relative to the syringe barrel (e.g., to discharge fluid from the syringe, for instance when installed on a power injector). The coupling is detachably connectable to a power injector syringe mount. Moreover, the coupling is mounted to the power injector syringe using at least the retention ring.

A second aspect of the present invention is embodied by a power injector syringe assembly that includes a power injector syringe and a coupling. The power injector syringe includes a syringe barrel, a syringe flange, and a plunger that is movable relative to the syringe barrel (e.g., to discharge fluid from the syringe, for instance when installed on a power injector). The coupling is detachably connectable to a power injector syringe mount. Moreover, the coupling and power injector syringe are permanently joined or connected.

A number of feature refinements and additional features are separately applicable to each of the first and second aspects of the present invention. These feature refinements and additional features may be used individually or in any combination. The following discussion is separately applicable to each of the first and second aspects, up to the start of the discussion of a third aspect of the present invention. Initially, any of the features of the first aspect may be used by the second aspect, and vice versa. The first and second aspects may also be used in combination.

A permanent connection may be utilized between the coupling and the power injector syringe, which may be separately fabricated components. Any appropriate way of providing this permanent connection may be utilized, for instance RF welding, sonic welding, adhesive bonding, heat staking, ultrasonic welding, a snap fit connection, an interference fit connection, mechanical fasteners, or any combination thereof. A permanent coupling, connection, joined state, or the like between the power injector syringe and the coupling may be characterized as one in which at least one of the coupling and the power injector syringe would be damaged if an attempt were made to disassemble or detach the coupling from the power injector syringe. Another characterization is that the power injector syringe may not be intended to be removed from the coupling in the case where a permanent connection or the like exists between these two components (e.g., it may be such that the coupling and power injector syringe are not detachably interconnected). Although the power injector syringe and the coupling may be maintained in a fixed relative position to each other if permanently joined, the power injector syringe and the coupling could be movable relative to each other in at least some respect even if these two components are permanently joined.

The syringe flange may be disposed inside the coupling when the power injector syringe and coupling are in an assembled or joined state. An end of the power injector syringe having the syringe flange may be directed through an open end of the coupling (e.g., a syringe end of the coupling) to assemble the power injector syringe and coupling. In one embodiment, the syringe flange engages a syringe flange seat that is located inside the coupling. This syringe flange seat may be of any appropriate configuration, and may extend from an inner wall of the coupling that defines an opening or passageway that may extend completely through the coupling. In one embodiment, the syringe flange seat is an annular structure. In another embodiment, the syringe flange seat includes a plurality of segments that are spaced about an inner wall of the coupling at a common position along the length of an opening or passageway that may proceed through the coupling.

A retention ring may be used to mount the coupling to the power injector syringe, including where the coupling and power injector syringe are permanently joined or connected. The coupling, power injector syringe, and retention ring may be three separate components that are separately positioned to assemble the power injector syringe assembly. In an assembled state or configuration for the power injector syringe assembly, the coupling and the retention ring may interface with opposite end surfaces of the syringe flange of the power injector syringe. The above-noted syringe flange seat of the coupling and the retention ring may be positioned on opposite sides of the syringe flange of the power injector syringe in the assembled state or configuration for the power injector syringe assembly. In one embodiment, the retention ring extends within the coupling. In one embodiment, a first retention ring portion or section is disposed within the coupling (e.g., in abutting relation with the one end face of the syringe flange of the power injector syringe), while a second retention ring portion or section is disposed beyond the adjacent end of the coupling (e.g., the syringe end).

The coupling may utilize a one-piece or integral construction (e.g., in the form of a unitary part). The coupling itself may lack any joint of any kind. The coupling may also be characterized as lacking any moving part. Any appropriate material or combination of materials may be used to define the coupling, and the coupling may be fabricated in any appropriate manner. Representative materials from which the coupling may be formed include without limitation aluminum, steel, polycarbonate, polyester, PP, PET, PBT, PE, and other suitable plastics.

The coupling may include a coupling flange. An inward (relative to a central longitudinal axis of the power injector syringe assembly) portion of the coupling flange may define the above-noted syringe flange seat, although the coupling flange and the syringe flange seat could be different structures. The coupling flange is subject to a number of characterizations. One function that may be provided by the coupling flange is to provide at least somewhat of a fluid seal or fluid impediment when mounted to the power injector (e.g., functioning as a "drip flange"). The coupling flange may be an annular structure, extending a full 360° about a central longitudinal axis extending through the coupling and which may coincide with a fluid passageway through the coupling (e.g., the coupling may be concentrically disposed about this central longitudinal axis). The coupling flange may be in the form of a disk-shaped structure. The coupling flange has a maximum thickness within a range of 0.010" to 0.020" in one embodiment, and a maximum thickness of 0.5" in another embodiment (e.g., measured along the central longitudinal axis).

An outer diameter of the coupling flange may be of a fixed amount or value (e.g., the coupling flange need not incorporate a syringe clamping or engaging structure that moves orthogonally to a central longitudinal axis of the coupling to facilitate retention of a power injector syringe within the coupling). The coupling flange, as well as the entirety of the coupling, may be of an integral construction. A perimeter of the coupling flange (e.g., in the form of a circular configuration) may define a maximum outer diameter of the coupling.

The coupling flange may be characterized as separating the coupling into first and second cylindrical sections (e.g., sections of the coupling that have an outer, cylindrical surface). First and second cylindrical sections may be disposed on opposite sides of the coupling flange. The first and second cylindrical sections may extend in opposite directions from the coupling flange. In one embodiment, the first cylindrical section is on a power injector side of the coupling flange (e.g., the first cylindrical section may extend from the coupling flange in the direction of the power injector when the coupling is installed thereon), while the second cylindrical section is on a power injector syringe side of the coupling flange (e.g., the second cylindrical section may extend from the coupling flange away from the power injector when the coupling is installed thereon).

The above-noted first and second cylindrical sections may have different outer diameters. In one embodiment, the first cylindrical section has a smaller outer diameter than the second cylindrical section. The first cylindrical section may correspond with an engaging structure of a syringe mount when the power injector syringe assembly is installed on a power injector. The second cylindrical section may be sized to accommodate a positioning of the syringe flange of the power injector syringe within the coupling. In one embodiment, the second cylindrical section is the only portion of the coupling that is disposed on a power injector syringe side of the coupling flange. One embodiment has a maximum length of the second cylindrical section being 0.140", and another embodiment has this maximum length being 0.5" (e.g., measured along the central longitudinal axis of the coupling).

A perimeter of the coupling may include at least one mounting flange. The above-noted first cylindrical section may extend from the coupling flange to such a mounting flange. In any case, one embodiment has the mounting flange being in the form of an annular structure, extending a full 360° about the central longitudinal axis of the coupling. Another embodiment utilizes a plurality of mounting flanges that are spaced about the central longitudinal axis of the coupling at a common location along this central longitudinal axis.

Each/any mounting flange utilized by the coupling may facilitate the installation of the power injector syringe assembly on a syringe mount of a power injector. The following discussion is applicable to each mounting flange utilized by the coupling. The mounting flange may be characterized as having a wedge-shaped cross-section (e.g., in a cross-sectional view taken along/through the central longitudinal axis of the coupling). Another characterization is that an outer diameter of the mounting flange increases (e.g., continually) proceeding in the direction of the coupling flange or a syringe end of the coupling (or proceeding in a direction that is away from a power injector end of the coupling). Yet another characterization is that the mounting flange utilizes at least two different outer diameters along its length dimension (such a length dimension may coincide with the central longitudinal axis of the coupling). The mounting flange may also be characterized as a cam—a structure that facilitates movement of another structure (e.g., a cam follower) when engaged therewith and when moved in an appropriate manner.

The coupling of the power injector syringe assembly may be used to install the same on a syringe mount of a power injector. This syringe mount may include a syringe retainer (e.g., a flex ring) and a syringe retainer actuator (e.g., a rotating ring). The mounting flange(s) of the coupling may engage and expand the syringe retainer as the power injector syringe assembly is moved relative to the power injector (e.g., axially, for instance along an axis that a syringe plunger driver or ram of the power injector moves during operation of the power injector) during installation of the power injector syringe assembly on the power injector. A subsequent contraction of the syringe retainer may occur once the mounting flange(s) has moved past the syringe retainer, for instance due to the elasticity or elastic nature of the syringe retainer, and which may then retain the power injector syringe assembly on the power injector in at least some respect. The coupling may include a coupling member (e.g., one or more projections on a perimeter thereof) that may engage a corresponding coupling member of the syringe retainer actuator (e.g., one or more slots or grooves that exist on an inner wall of the syringe retainer actuator). Rotation of the power injector syringe assembly while these coupling members are engaged may be used to rotate the syringe retainer actuator. Rotation of the syringe retainer actuator may be used to expand the syringe retainer to allow the power injector syringe assembly to be removed from the syringe mount (e.g., by an axial motion, for instance along an axis that a syringe plunger driver or ram of the power injector moves during operation of the power injector).

A third aspect of the present invention is embodied by a power injector syringe assembly that includes a power injector syringe receiver and a coupling. The power injector syringe receiver extends along a central longitudinal axis and coincides with at least a syringe barrel of a power injector syringe when installed in the power injector syringe receiver. For instance, the power injector syringe receiver may be at least as long as the syringe barrel. The coupling is interconnected with the power injector syringe receiver, and is also detachably connectable to a power injector syringe mount. The coupling includes at least one mounting flange and a first coupling member. At least two different outer diameters exist for the mounting flange proceeding along the longitudinal axis.

A fourth aspect of the present invention is embodied by a power injector syringe assembly that includes a power injector syringe receiver and a coupling. The power injector syringe receiver extends along a central longitudinal axis, and includes a first section and a syringe retention section that extend along different portions of the central longitudinal axis. The first section of the power injector syringe receiver extends no more than 180° about the central longitudinal axis, while its syringe retention section extends more than 180° about the central longitudinal axis. The coupling is interconnected with the power injector syringe receiver, and is also detachably connectable to a power injector syringe mount.

A fifth aspect of the present invention is embodied by a power injector syringe assembly that includes a power injector syringe receiver and a coupling. The power injector syringe receiver includes an end section or wall, along with an elongated and arcuate sidewall that extends along a central Longitudinal axis to the end wall. The power injector syringe receiver further includes a first section and a syringe retention section that extend along different portions of the central longitudinal axis. The first section extends no more than 180° about the central longitudinal axis, while the syringe retention section extends more than 180° about the central longitudinal axis. The coupling is interconnected with the power injector syringe receiver, and is also detachably connectable to a power injector syringe mount.

A number of feature refinements and additional features are separately applicable to each of the third, fourth, and fifth aspects of the present invention. These feature refinements and additional features may be used individually or in any combination. The following discussion is separately applicable to each of the third, fourth, and fifth aspects. Initially, any of the features of the third aspect may be used by each of the fourth and fifth aspects, any of the features of the fourth aspect may be used by each of the third and fifth aspects, and any of the features of the fifth aspect may be used by each of the third and fourth aspects. Any two or more of the third, fourth, and fifth aspects may also be used in combination.

The power injector syringe assembly may utilize a one-piece or integral construction (e.g., may be in the form of a unitary part). Alternatively, the coupling and the power injector syringe receiver may be separately formed and thereafter joined together (e.g., via a permanent connection). There may be a lack of a joint of any kind between the power injector syringe receiver and the coupling. The power injector syringe assembly may also be characterized as lacking any part that moves other than be a deflection or flexing. In one embodiment, the power injector syringe assembly includes only the power injector syringe receiver and the coupling.

The power injector syringe receiver may be characterized as extending from the coupling. An upper section of the power injector syringe receiver may be open to accommodate installing a power injector syringe into the power injector syringe receiver, as well as for removing the power injector syringe from the receiver. The opening in the power injector syringe receiver may exist at all times. A power injector syringe may be installed in this opening by maintaining a parallel relationship between the syringe and the syringe receiver while moving the syringe toward the receiver (e.g., within a vertical dimension if the length dimension of the power injector syringe receiver is in a horizontal dimension). A power injector syringe may also be installed in the power injector syringe receiver with its flange end being initially spaced further from the receiver than its nozzle end (e.g., with the long axes of these two components being in a skewed relation), and then sliding a forward portion of the syringe along the power injector syringe receiver to dispose this forward portion of the syringe under a syringe retention section of the power injector syringe receiver. The long axis of the syringe and the long axis of the power injector syringe receiver may each be at least substantially maintained in their respective orientations as the forward portion of the syringe is advanced relative to the power injector syringe receiver and until the syringe flange is aligned with the receiver, at which time the syringe flange end of the syringe may be directed into the power injector syringe flange receiver to dispose these two components in parallel relation.

The power injector syringe receiver may include one or more slots (e.g., in a sidewall or base of the receiver). Any appropriate number of slots may be utilized. In one embodiment, three slots are utilized. At least a majority of each slot may extend parallel to the central longitudinal axis. Each such slot may extend along a majority of the length of the power injector syringe receiver.

The power injector syringe receiver may include an end section or wall, along with an elongated and arcuate sidewall that extends along the central longitudinal axis to this end wall. The end section of the power injector syringe receiver may be frustumly-shaped to correspond with a frustumly-shaped end portion of a power injector syringe to be detachably positioned in the power injector syringe receiver. An aperture may extend through this end wall to accommodate a nozzle of a power injector syringe detachably positioned in the power injector syringe receiver.

The power injector syringe receiver may include a first section that extends no more than 180° about a central longitudinal axis of the power injector syringe assembly (e.g., where this axis coincides with an opening or passageway extending through the coupling). The first section of the power injector syringe receiver may extend from an end of the coupling (e.g., a power injector syringe end of the coupling). The power injector syringe receiver may include a syringe retention section that extends more than 180° about the central longitudinal axis of the power injector syringe assembly.

Both a first section and syringe retention section may be utilized by the power injector syringe receiver. The first section of the power injector syringe receiver may be located between the coupling and the syringe retention section of the power injector receiver, relative to the central longitudinal axis of the power injector syringe assembly. In one embodiment, the syringe retention section of the power injector syringe receiver extends a sufficient distance along the central longitudinal axis of the power injector syringe assembly to retain the syringe within the power injector syringe receiver during operation of a power injector that incorporates the power injector syringe assembly.

The coupling associated with the third, fourth, and fifth aspects may be in accordance with the coupling discussed above in relation to the first and second aspects, including in relation to how the same may interface or interact with a syringe mount of a power injector. However, the coupling of the third, fourth, and fifth aspects may terminate at the above-noted coupling flange. That is, the coupling used by the third, fourth, and fifth aspects may eliminate the above-noted second cylindrical section.

A number of feature refinements and additional features are separately applicable to each of above-noted first, second, third, fourth, and fifth aspects of the present invention. These feature refinements and additional features may be used individually or in any combination in relation to each of the above-noted first, second, third, fourth, and fifth aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector coupling includes "a mounting flange" alone does not mean that the power injector coupling includes only a single mounting flange). Moreover, any failure to use phrases such as "at least one" also does not limit the corresponding feature to the singular (e.g., indicating that a power injector coupling includes "a mounting flange" alone does not mean that the power injector coupling includes only a single mounting flange). Use of the phrase "at least generally" or the like in relation to a particular feature encompasses the corresponding characteristic and insubstantial variations thereof (e.g., indicating that a syringe barrel is at least generally cylindrical encompasses the syringe barrel being cylindrical). Finally, a reference of a feature in conjunction with the phrase "in one embodiment" does limit the use of the feature to a single embodiment.

As used herein, the term "detachably interconnected" describes a relationship between components where the components are interconnected yet retain the ability to be detached from each other where, after detaching, each of the components remains in a usable condition. For example, a coupling being detachably connected to or interconnected with a power injector describes a condition where the coupling is currently installed on the power injector (e.g., in a manner where power injector supports the coupling) in a configuration that is usable by the power injector. Furthermore, after being detached, each of the coupling and power injector retains the ability to be once again detachably interconnected.

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical imaging application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging) and/or any appropriate medical diagnostic and/or therapeutic application (e.g., injection of chemotherapy, pain management, etc.). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, therapeutic fluid, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

BRIEF DESCRIPTION OF THE FIGURES

FIG. 3 is an exploded, perspective view of one embodiment of a power injector syringe assembly where a power injector syringe and coupling are permanently joined.

FIG. 6 is a perspective view of a syringe end of the power injector coupling used by the power injector syringe assembly of FIGS. 3 and 4.

FIG. 7 is a perspective view of a power injector end of the power injector coupling used by the power injector syringe assembly of FIGS. 3 and 4.

FIG. 20 is a side view of the power injector syringe assembly of FIG. 12.

FIG. 21 is a top view of the power injector syringe assembly of FIG. 12.

FIG. 22 is a bottom view of the power injector syringe assembly of FIG. 12.

DETAILED DESCRIPTION

Figure 1:
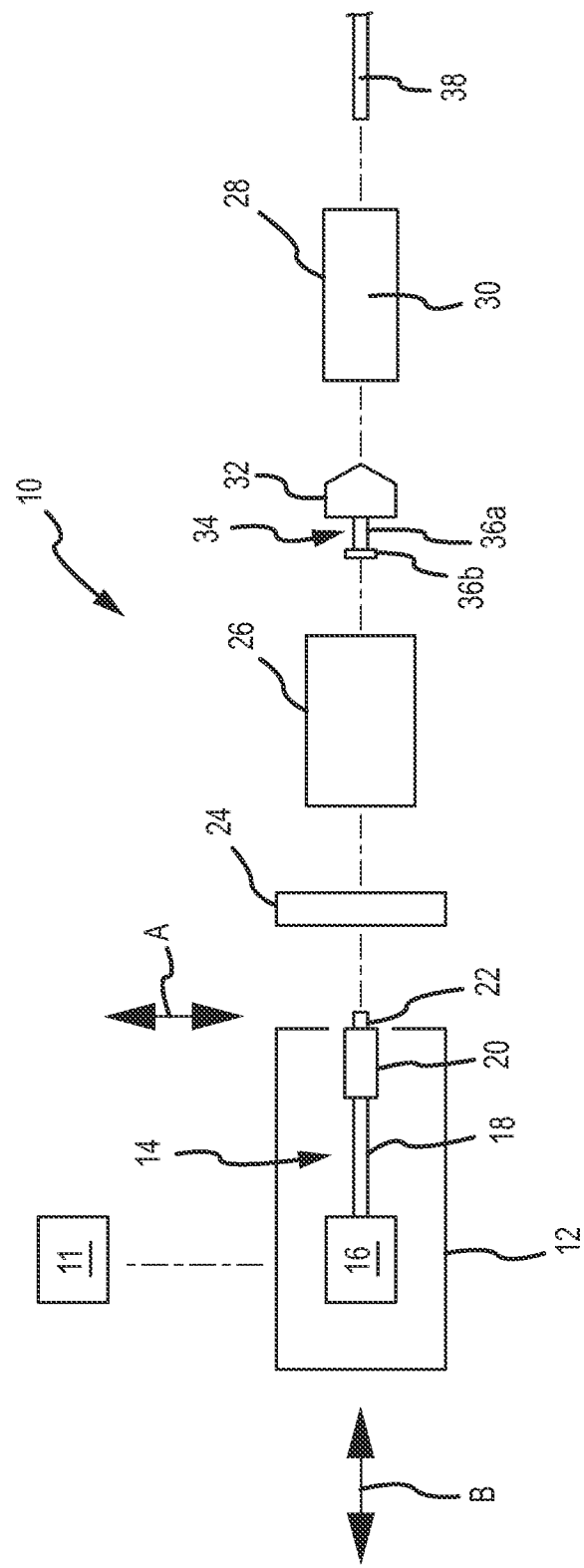
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing.

Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
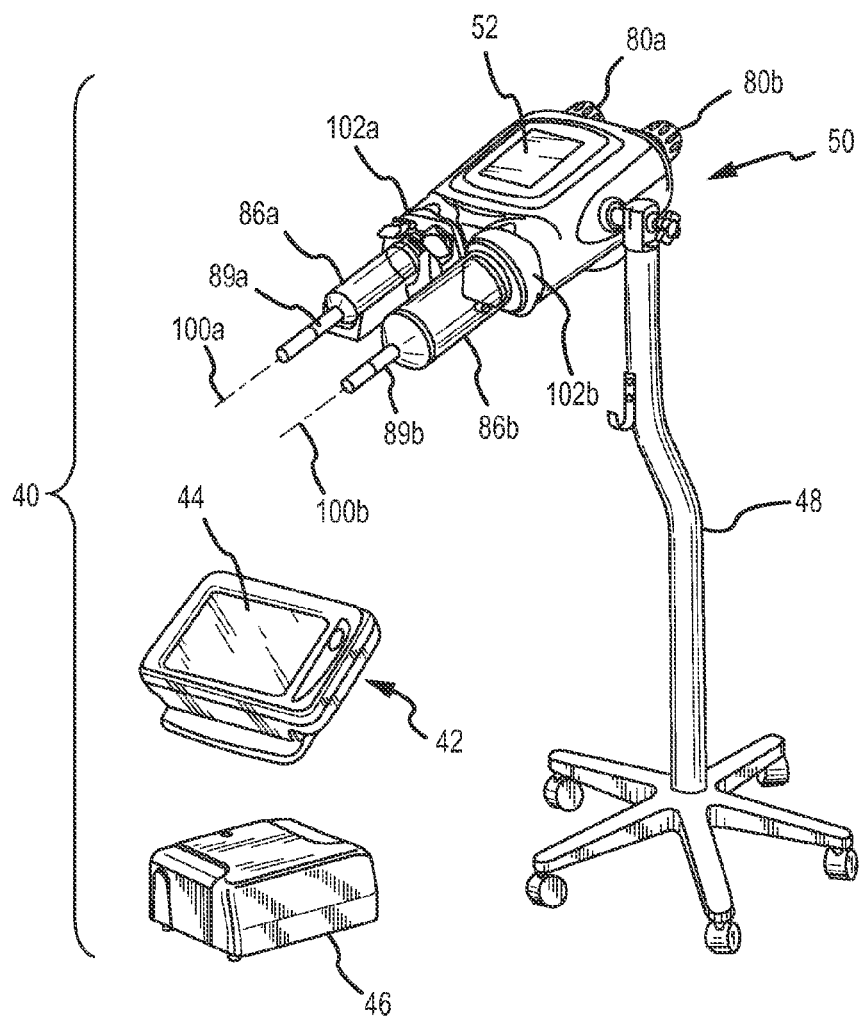
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. Two syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following arid in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
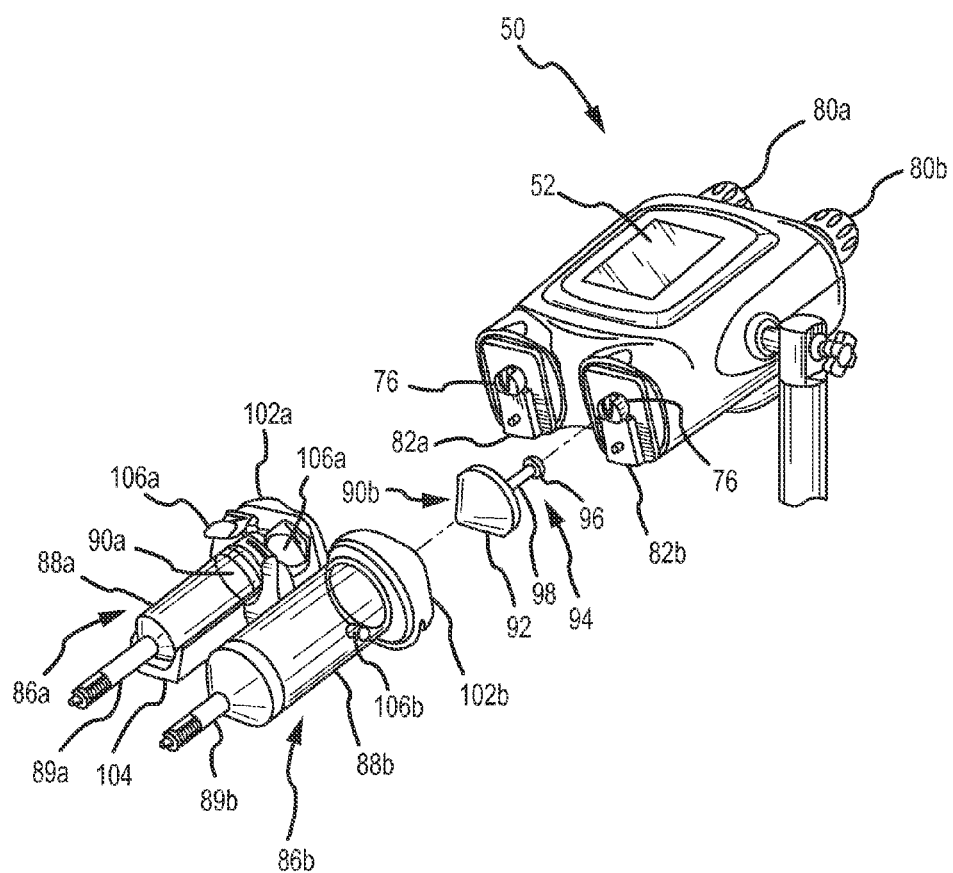
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2O) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
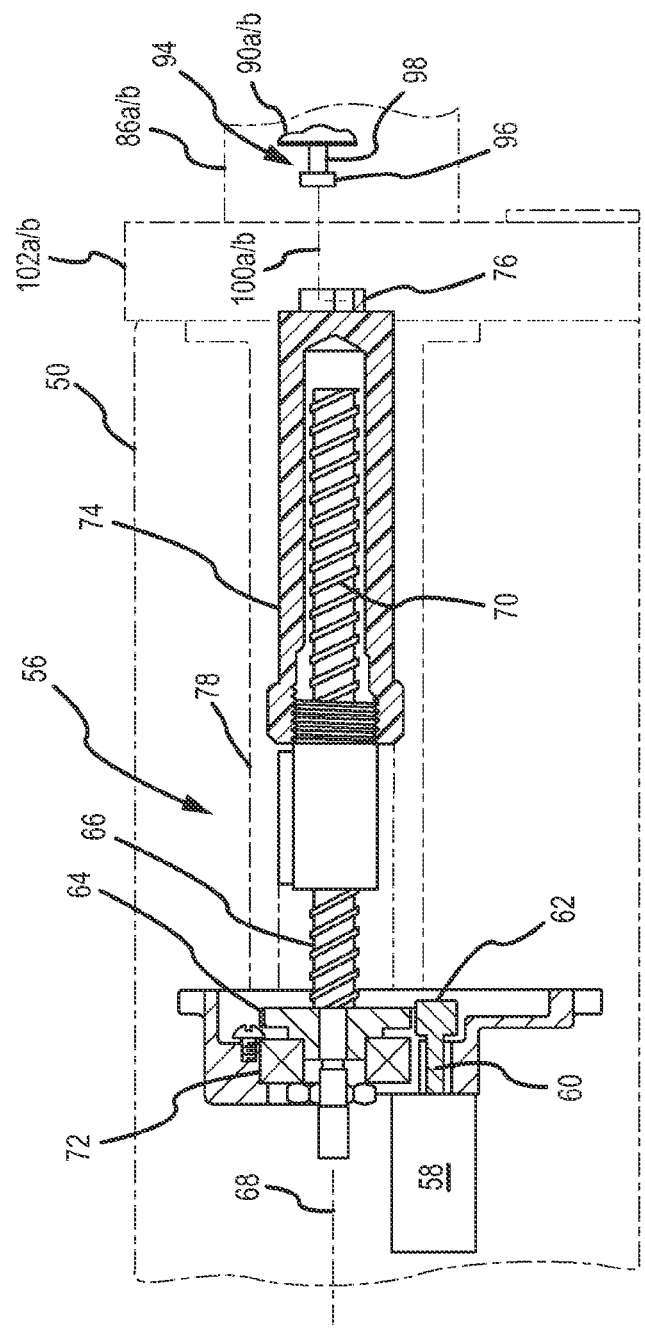
FIG. 2C is a schematic of one embodiment of a syringe plunger drive assembly used by the power injector of FIG. 2A.
Figure 4:
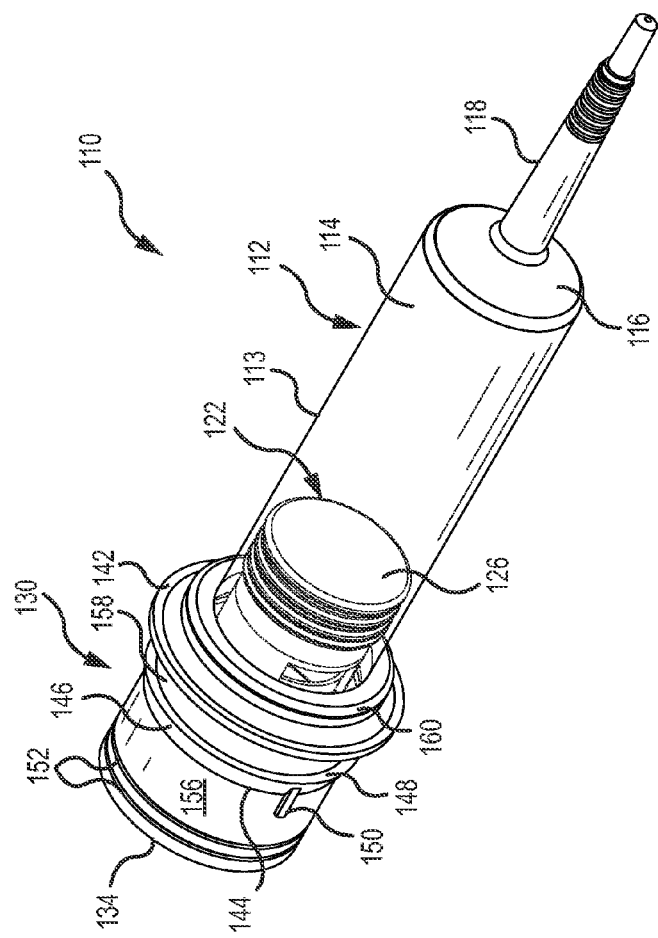
FIG. 4 is a perspective view of the power injector syringe assembly of FIG. 3 in an assembled state.
Figure 5:
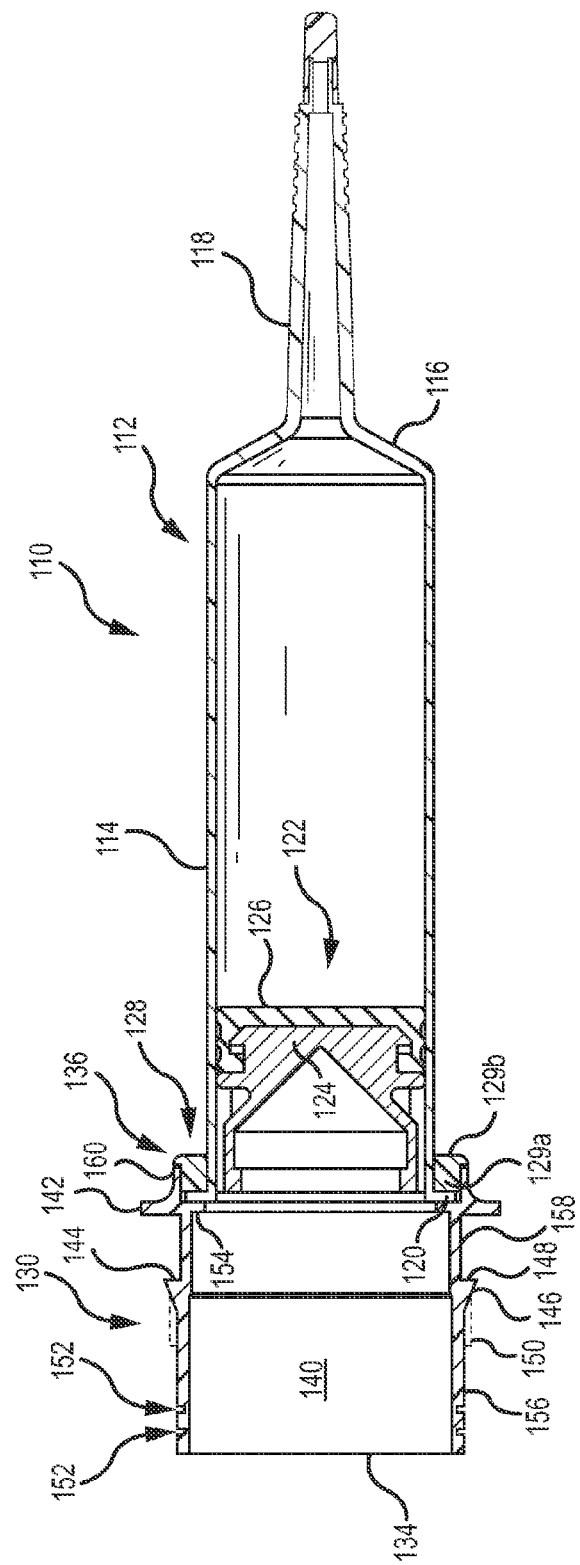
FIG. 5 is a cross-sectional view of the power injector syringe assembly of FIG. 4, taken along its length dimension.
Figure 9:
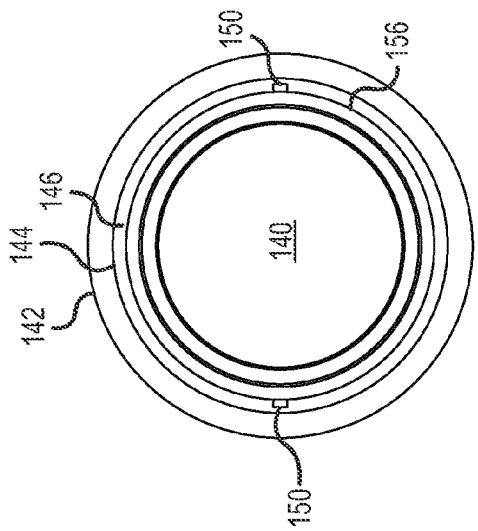
FIG. 9 is an end view of the power injector end of the power injector coupling used by the power injector syringe assembly of FIGS. 3 and 4.
Figure 11:
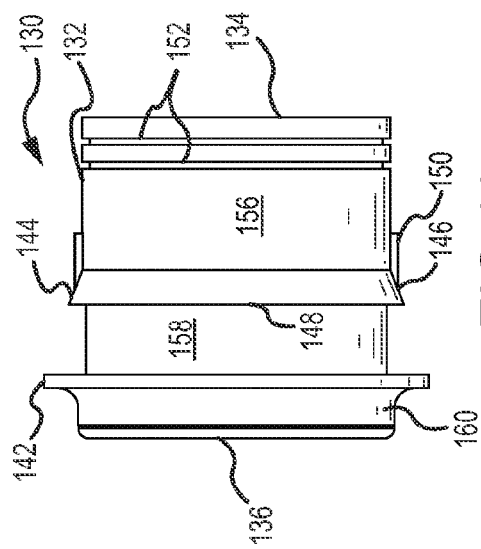
FIG. 11 is another side view of the power injector coupling used by the power injector syringe assembly of FIGS. 3 and 4.
Figure 10:
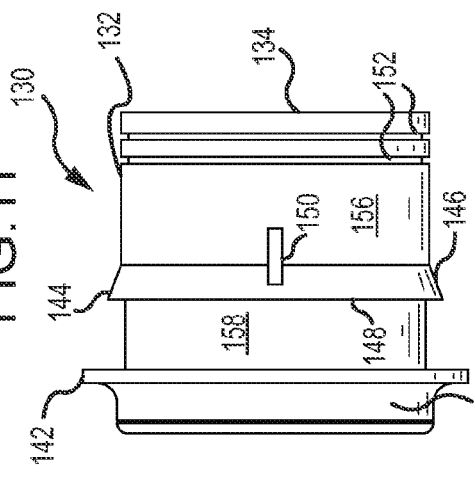
FIG. 10 is one side view of the power injector coupling used by the power injector syringe assembly of FIGS. 3 and 4.
Figure 8:
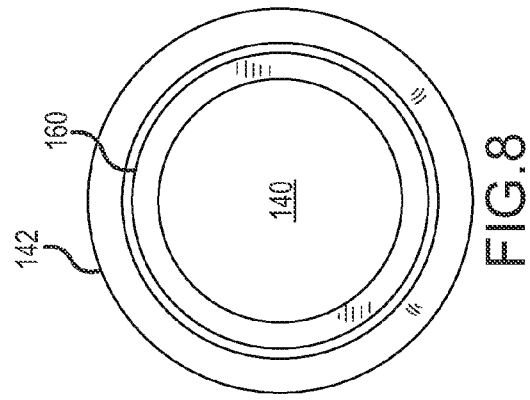
FIG. 8 is an end view of the syringe end of the power injector coupling used by the power injector syringe assembly of FIGS. 3 and 4.
Figure 12:
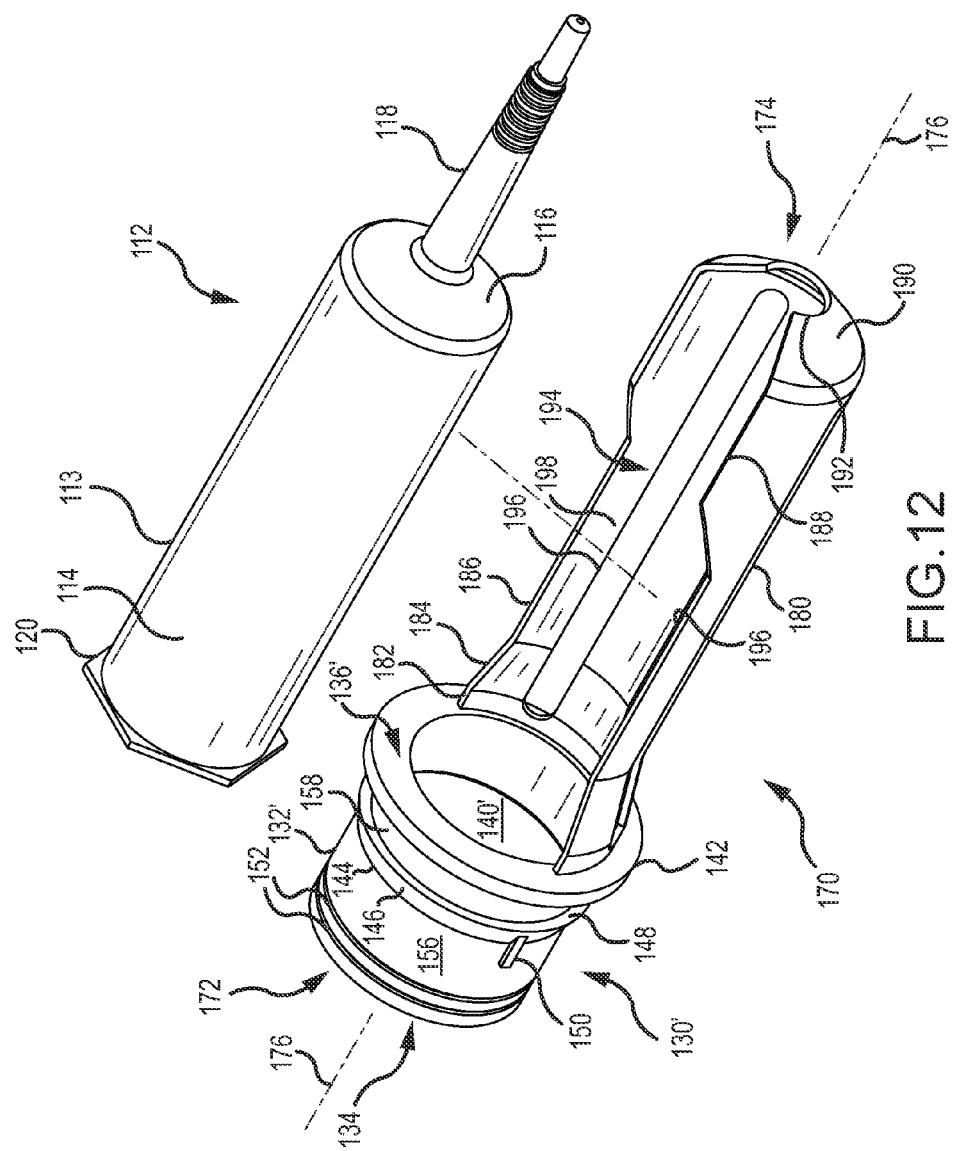
FIG. 12 is a perspective top view (from a syringe end) of another embodiment of a power injector syringe assembly that incorporates a syringe cradle and a coupling that may be integrally formed, and with a power injector syringe being positioned for installation in the cradle.
Figure 13:
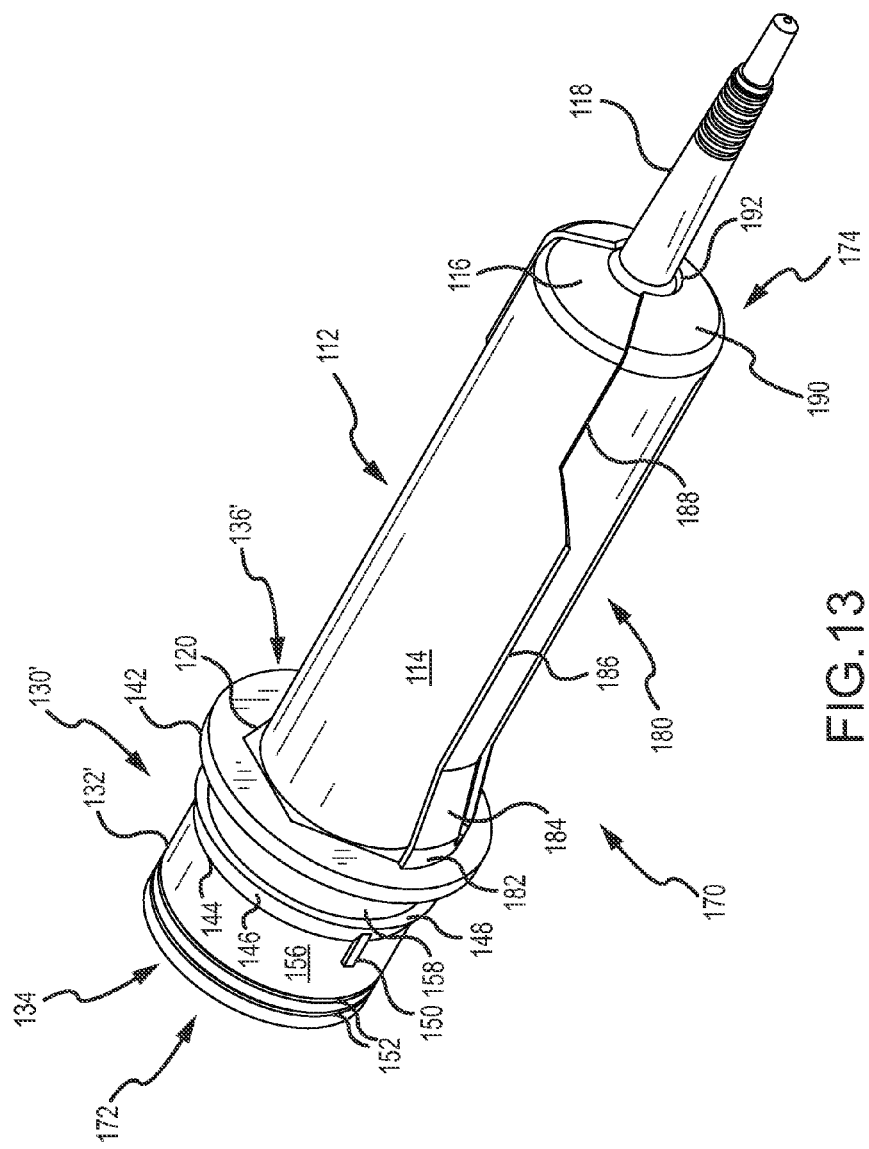
FIG. 13 is a perspective top view (from the syringe end) of the power injector syringe assembly of FIG. 12, with a power injector syringe having been installed therein.
Figure 14:
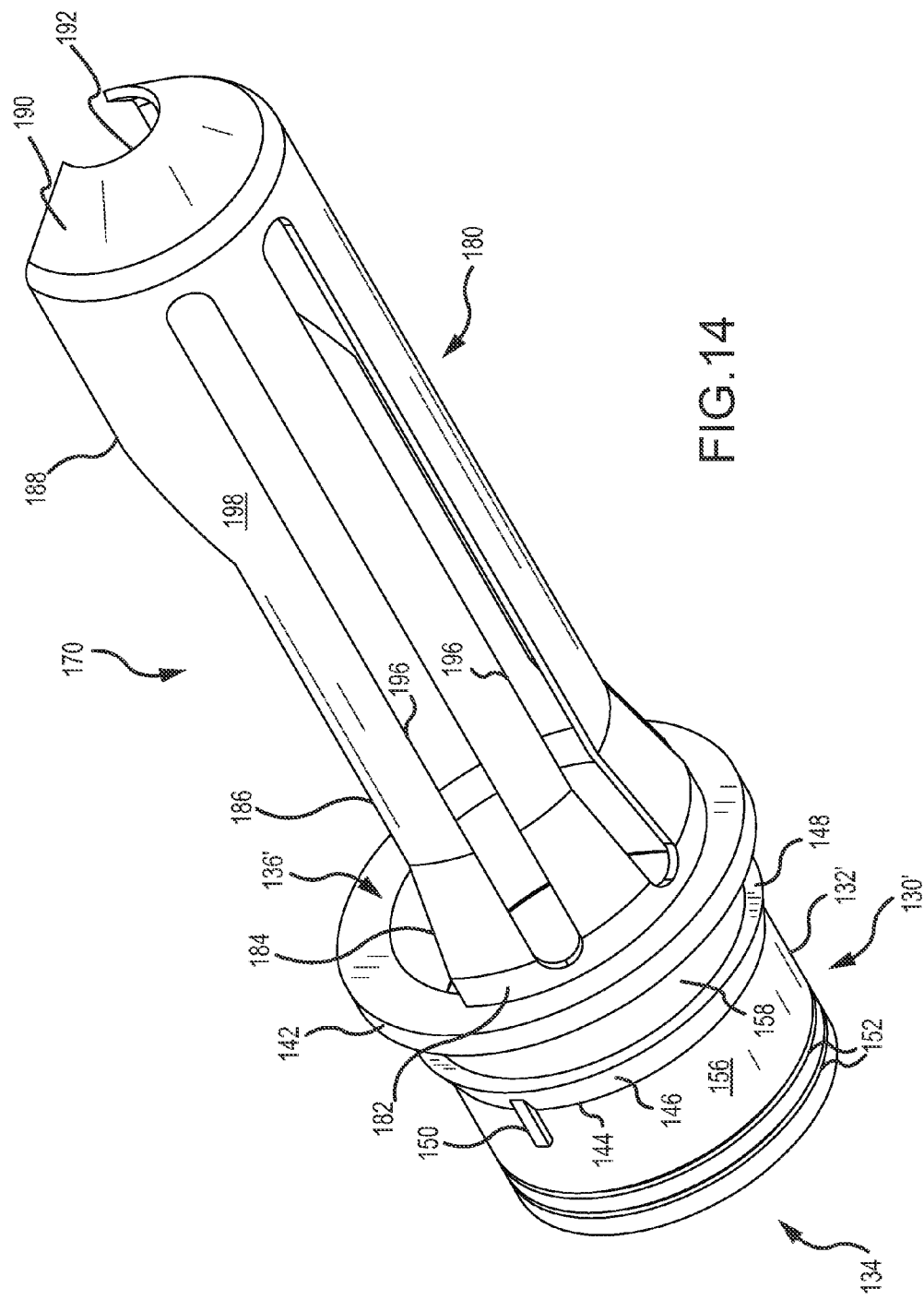
FIG. 14 is a perspective bottom view of an underside of the power injector syringe assembly of FIG. 12.
Figure 15:
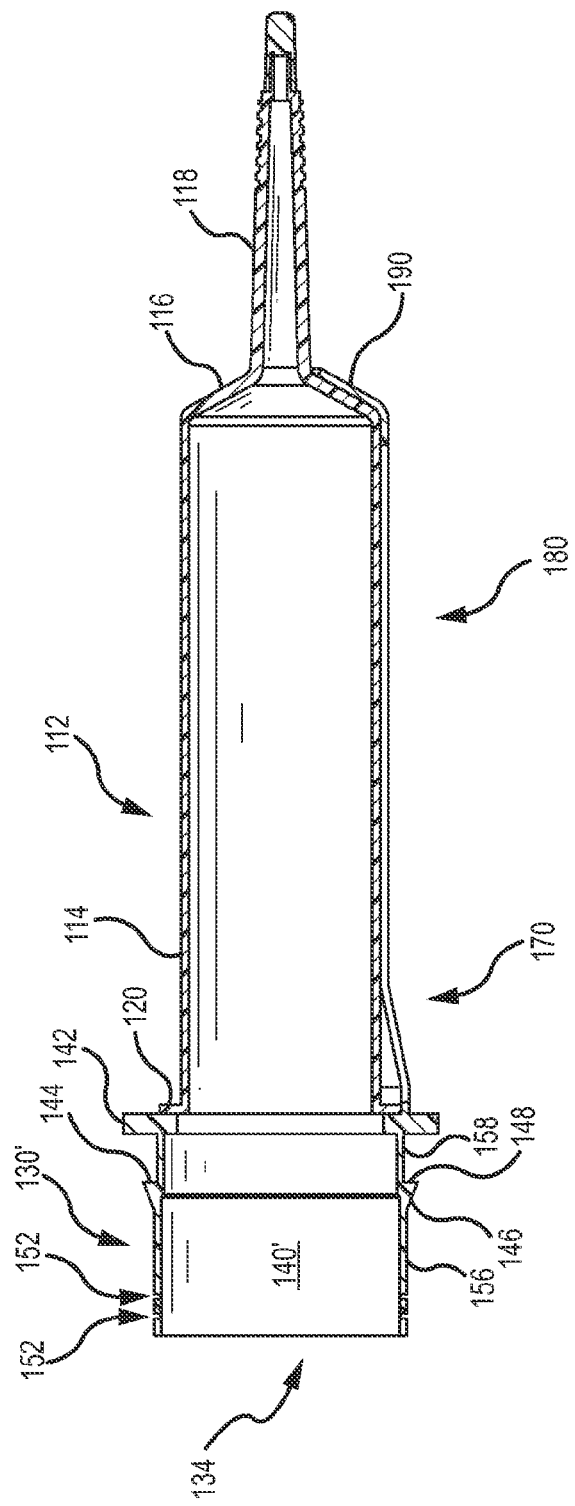
FIG. 15 is a cross-sectional view of the power injector assembly of FIG. 12 taken along its long axis, with a power injector syringe installed therein.
Figures 16, 17:
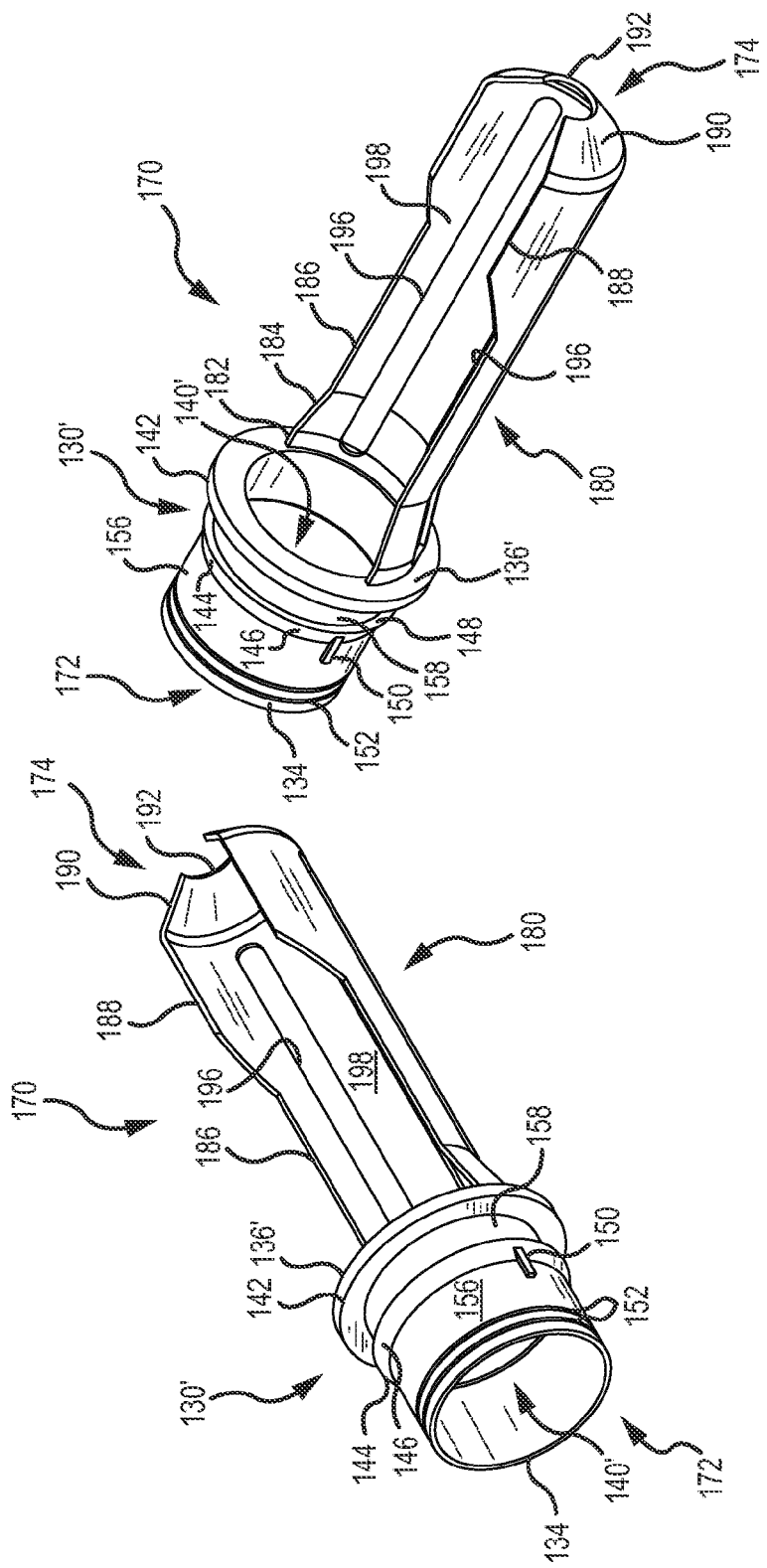
FIG. 16 is a perspective top view (from a power injector end) of the power injector syringe assembly of FIG. 12.
FIG. 17 is a perspective top view (from a syringe end) of the power injector syringe assembly of FIG. 12.
Figure 19:
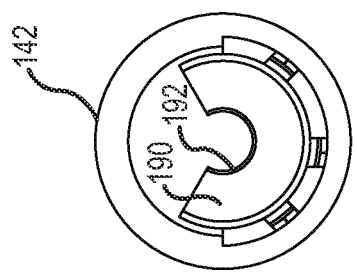
FIG. 19 is an end view of a syringe end of the power injector syringe assembly of FIG. 12.
Figure 18:
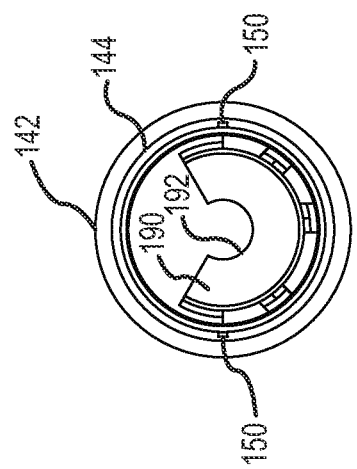
FIG. 18 is an end view of a power injector end of the power injector syringe assembly of FIG. 12.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

One embodiment of what may be characterized as a power injector syringe assembly is illustrated in FIGS. 3-11 and is identified by reference numeral 110. The power injector syringe assembly 110 generally includes a power injector syringe 112 and a power injector coupling 130, and may be collectively installed (e.g., installed as a single unit) on a power injector in a manner that will be discussed below in relation to FIGS. 25-26. Generally, the power injector syringe 112 is permanently mounted, joined, or affixed to the coupling 130. Any appropriate permanent connection between the power injector syringe 112 and the power injector coupling 130 may be utilized (e.g., RF welding, sonic welding, adhesive bonding, ultrasonic welding, heat staking, a snap/interference fit, mechanical fasteners, or any combination thereof). Being permanently mounted, joined, or affixed means that the power injector syringe 112 is not intended to be separated from the power injector coupling 130 without damaging at least one of the power injector syringe 112 or the power injector coupling 130.

Any appropriate configuration may be utilized by the power injector syringe 112. In the illustrated embodiment, the power injector syringe 112 includes a syringe body 113. This syringe body 113 may be of any appropriate configuration, and in the illustrated embodiment includes a syringe flange 120 on one end thereof (and which may be of any appropriate configuration), a syringe barrel 114 (e.g., a cylindrical perimeter) that extends from this syringe flange 120, a tapered, frustumly-shaped, or frusto-conical transition section 116 that extends from the syringe barrel 114 (e.g., tapering inwardly toward a central longitudinal axis 138 of the power injector syringe assembly 110 progressing from the syringe barrel 114 toward a nozzle 118 of the syringe 112), and a nozzle 118 that extends from the transition section 116. Tubing (not shown) may be mounted to the nozzle 118 in any appropriate manner (e.g., by the nozzle 118 including a connector or any other appropriate structure for interfacing with the desired tubing).

A plunger 122 of any appropriate configuration is movable relative to the syringe body 113 and is at least partially disposed within the syringe body 113. In the illustrated embodiment, the plunger 122 is of a two-piece construction, being in the form of a plunger body 124 and a plunger head or cap 126. The plunger body 124 may be configured to interface or interconnect with a power injector ram, while the plunger cap 126 interfaces with liquid contained within the syringe body 113. The plunger cap 126 may be mounted to the plunger body 124 in any appropriate manner (e.g., using a snap-fit connection). Although the plunger cap 126 is illustrated as having a flat end to interface with liquid contained within the syringe body 113, other configurations could be utilized (e.g., conical).

The power injector coupling 130 allows the power injector syringe assembly 100 to be installed on a certain power injector, and may be characterized as being disposed on an end of the power injector syringe 112. It should be noted that the power injector syringe 112, by itself (i.e., without being integrated into the power injector syringe assembly 110) may be configured to work with one power injector configuration. However, when the power injector syringe 112 is used in combination with the power injector coupling 130 to define the power injector syringe assembly 110, the power injector syringe 112 may be used with a different power injector configuration. That is, the power injector syringe 112 may be directly detachably mounted to a syringe mount on a power injector of one configuration, but may require the power injector coupling 130 to be detachably mounted to a syringe mount of a different power injector configuration.

The power injector coupling 130 may be of an integral or one-piece construction. That is, the power injector coupling 130 may be configured such that there are no joints of any kind between any adjacent portions of the power injector coupling 130. The power injector coupling 130 may also be characterized as lacking any parts that move other than by flexure or deflection. Although the power injector coupling 130 may be formed from any appropriate material or combination of materials, in one embodiment the power injector coupling 130 is fabricated from materials such as aluminum, steel, polycarbonate, polyester, PP, PET, PBT, PE, and other suitable plastics.

The power injector coupling 130 may be characterized as including a body 132, which in turn has a first end 134 (e.g., a power injector end) and a second end 136 (e.g., a syringe end) that are spaced along a central longitudinal axis 138 of the power injector syringe assembly 110. An opening or passageway 140 extends completely through the power injector coupling 130 along the central longitudinal axis 136, or between its first/power injector end 134 and its second/syringe end 136. A ram of a power injector may extend through this opening 140 to interact (e.g., interface and/or detachably interconnect) with the plunger 122 of the power injector syringe 112 so as to be able to move the plunger 122 relative to the syringe body 113 in at least one direction (e.g., on a discharge stroke, or where the plunger 122 is advanced toward the syringe nozzle 118). The body 132 of the power injector coupling 130 may include one or more encoding elements 152 of any appropriate type and that may be utilized to identify one or more characteristics of the power injector syringe 112 to the power injector (e.g., the power injector may "read" the encoding element(s)152 in any appropriate manner, including optically, mechanically, etc).

A coupling flange 142 is disposed toward the second or syringe end 136 of the power injector coupling 130. The coupling flange 142 may be characterized as a drip flange 142—functioning to provide at least somewhat of a fluid barrier or impediment to fluid movement when the power injector syringe assembly 110 is mounted to a power injector via the power injector coupling 130. In any case, the coupling flange 142 is subject to a number of structural characterizations, which may apply individually or in any combination: 1) the coupling flange 142 may have an annular configuration—extending a full 360° about the central longitudinal axis 138; 2) the coupling flange 142 may have a fixed outer diameter; 3) the coupling flange 142 may have a circular perimeter; 4) a perimeter of the coupling flange 142 may define a maximum outer diameter of the power injector coupling 130; 5) the coupling flange 142 may have a maximum thickness within a range of 0.010" to 0.020" in one embodiment, and a maximum thickness of about 0.5" in another embodiment, where this maximum thickness is measured along or parallel to the central longitudinal axis 138; 6) the coupling flange 142 may be of an integral or one-piece construction (e.g., having no parts that move other than by flexure or deflection); and 7) the coupling flange 142 may be disk-shaped.

An inner edge of the coupling flange 142 may extend into the opening or central passageway 140 of the power injector coupling 130 to define a syringe flange seat 154. That is, an end of the syringe flange 120 may interface with or butt up against an end surface of the coupling flange 142 within the interior of the coupling 130. The syringe flange seat 154 could instead be a separate structure from the coupling flange 142. The syringe flange seat 154 and the coupling flange 142 may be disposed at the same position along the central longitudinal axis 138 as shown, or they could be disposed at different positions along the central longitudinal axis 138 (e.g., in the case where the syringe flange seat 154 is not part of the coupling flange 142).

The body 132 of the power injector coupling 130 also includes at last one mounting or retention flange 144 that is located between the coupling flange 142 and the first or power injector end 134 of the power injector coupling 130. In the illustrated embodiment, a single annular mounting flange 144 is utilized by the power injector coupling 130 ("annular" meaning that the mounting flange 144 extends a full 360° about the central longitudinal axis 138). As will be discussed below in relation to FIGS. 25-26, the mounting flange 144 is used to facilitate the installation of the power injector syringe assembly 110 onto a power injector. In this regard, the mounting flange 144 includes a sloped surface 146 and an end surface 148 that are disposed in different orientations. The sloped surface 146 slopes or tapers inwardly progressing in the direction of the first or power injector end 134 of the power injector coupling 130 (e.g., slopes or tapers outwardly progressing in the direction of the second or syringe end 136 of the power injector coupling 130), while the end surface 148 may be disposed perpendicularly to the central longitudinal axis 138 of the power injector syringe assembly 110 (although other orientations may be appropriate for the end surface 148 to secure the power injector syringe assembly 110 to the corresponding power injector). Generally, the end surface 148 may be oriented to resist movement of the power injector syringe assembly 110 relative to a power injector when installed thereon, where this movement is at least generally along the central longitudinal axis 138 (e.g., providing the function of an axial stop of sorts).

The mounting flange 144 may be characterized as having a wedge-shaped cross-section. Another characterization is that the mounting flange 144 may have an outer diameter that increases (e.g., continually) proceeding in the direction of the coupling flange 142 or the second/syringe end 136 of the coupling 130. Yet another characterization is that the mounting flange 144 includes at least two different outer diameters proceeding along the central longitudinal axis 138. The mounting flange 144 may be characterized as a cam—a structure that when moved facilitates a desired movement of another structure (e.g., movement of part of a syringe mount of a power injector in a manner that facilitates the installation of the power injector syringe assembly 110 on the power injector).

One or more coupling members 150 are incorporated by the power injector coupling 130 (e.g., on a perimeter thereof). As will be discussed below in relation to FIGS. 25-26, a coupling member 150 is used to facilitate the removal of the power injector syringe assembly 110 from a power injector (e.g., by interacting with a corresponding coupling member of an actuator of a power injector syringe mount that detachably receives the power injector syringe assembly 110). Each coupling member 150 may be of any appropriate configuration. In the illustrated embodiment, each coupling member 150 is in the form of a projection or raised structure (e.g., to interface with a groove or slot of an actuator of a power injector syringe mount, such that rotation of the power injector syringe assembly 110 will in turn rotate the actuator, which in turn will release the power injector syringe mount from the power injector syringe assembly 110). Any appropriate number of coupling members 150 may be utilized. Multiple coupling members 150 may be appropriately spaced about the central longitudinal axis 138. In the illustrated embodiment, each coupling member 150 is at least partially disposed on the mounting flange 144, and extends therefrom in the direction of the first or power injector end 134 of the power injector coupling 130.

The body 132 of the power injector coupling 130 may be characterized as including a first cylindrical section 156, a second cylindrical section 158, and a third cylindrical section 160. The second cylindrical section 158 is disposed between the first cylindrical section 156 and the third cylindrical section 160 relative to the central longitudinal axis 138. The first cylindrical section 156 may include the first or power injector end 134 (e.g., on a power injector side of the coupling flange 142), while the third cylindrical section 160 may include the second or syringe end 136 (e.g., on a power injector syringe side of the coupling flange 142). The encoding elements 152, the mounting flange 144, and each coupling member 150 may be incorporated by the first cylindrical section 156. The coupling flange 142 may separate the second cylindrical section 158 (e.g., on a power injector side of the coupling flange 142) from the third cylindrical section 160.

In one embodiment, the outer diameter of the third cylindrical section 160 of the power injector coupling 130 is larger than the outer diameter of each of the first cylindrical section 156 and the second cylindrical section 158. In one embodiment, the outer diameter of the second cylindrical section 158 is less than the outer diameter of the first cylindrical section 156. For instance, the second cylindrical section 158 may be used to secure the power injector syringe assembly 110 to a power injector syringe mount in a manner that will be discussed below.

The power injector syringe assembly 110 may also utilize a retention ring 128 to secure the power injector syringe 112 to the power injector coupling 130. In this regard, the syringe flange 120 may be directed through the second or syringe end 136 of the power injector coupling 130, into the opening 140, and ultimately into engagement with the syringe flange seat 154. The retention ring 128 may be positioned about the power injector syringe 112 and advanced relative to the power injector coupling 130 such that a first retention ring part 129a is also directed through the second or syringe end 136 of the power injector coupling 130, into the opening 140, and ultimately into engagement with the syringe flange 120. That is, the syringe flange 120 may be sandwiched between the syringe flange seat 154 of the power injector coupling 130 and the first retention ring part 129a of the retention ring 128. Although the entirety of the retention ring 128 could be disposed inside the power injector coupling 130, in the illustrated embodiment the retention ring 128 includes a second retention ring part 129b that is disposed beyond the second or syringe end 136 of the power injector coupling 130.

A permanent connection may exist between the power injector syringe 112, the power injector coupling 130, and the retention ring 128. Again, this permanent connection means that the power injector syringe 112, power injector coupling 130, and retention ring 128 are not intended for disassembly other than by damaging one or more of these components. RF welding, sonic welding, one or more adhesives (e.g., adhesive bonding), heat staking, a snap or interference fit, ultrasonic welding, one or more mechanical fasteners, or any combination thereof could be utilized to maintain a permanent connection between the power injector syringe 112, power injector coupling 130, and retention ring 128.

One embodiment of what may be characterized as a power injector syringe assembly is illustrated in FIGS. 12-22 and is identified by reference numeral 170. Generally, the power injector syringe assembly 170 may be detachably mounted to a power injector (e.g., in accordance with the subsequent discussion of FIGS. 25-26). The above-discussed power injector syringe 112 (or any other appropriate power injector syringe configuration) may be detachably received by the power injector syringe assembly 170, either before or after the power injector syringe assembly 170 has been mounted to the power injector. Contrary to the embodiment of FIGS. 3-11, the power injector syringe 112 is not a required component of the power injector syringe assembly 170 of FIGS. 12-22.

Generally, the power injector syringe assembly 170 provides an appropriate interface of sorts between the power injector syringe 112 and a certain power injector. It should be noted that the power injector syringe 112, by itself, may be configured to work with one power injector configuration. However, when the power injector syringe 112 is used in combination with the power injector syringe assembly 170, the power injector syringe 112 may be used with a different power injector configuration. That is, the power injector syringe 112 may be directly detachably mounted to a syringe mount on a power injector of one configuration, but may require the power injector syringe assembly 170 to be detachably mounted to a syringe mount of a different power injector configuration.

The power injector syringe assembly 170 may be of an integral or one-piece construction. That is, the power injector syringe assembly 170 may be configured such there are no joints of any kind between adjacent portions of the power injector syringe assembly 170. However, a coupling 130' and power injector syringe receiver 180 of the assembly 170 could be separately formed and then separately attached to one another (e.g., via a permanent connection). The power injector syringe assembly 170 may also be characterized as lacking any parts that move other than be flexure or deflection. Although the power injector syringe assembly 170 may be formed from any appropriate material or combination of materials, in one embodiment the power injector syringe assembly 170 may be fabricated from materials such as aluminum, steel, polycarbonate, polyester, PP, PET, PST, PE, and other suitable plastics.

The power injector syringe assembly 170 includes a first or power injector end 172 and a second or syringe nozzle end 174 that are spaced along a central longitudinal axis 176 of the power injector syringe assembly 170. Generally, the power injector syringe assembly 170 includes a syringe cradle or power injector syringe receiver 180, along with a variation of the power injector coupling 130 discussed above in relation to the embodiment of FIGS. 3-11. The power injector mounting section or power injector coupling 130' used by the power injector syringe assembly 170 is different from the above-discussed power injector coupling 130. Corresponding components between the power injector couplings 130 and 130' are identified by the same reference numeral, and the discussion presented above remains equally applicable. Those corresponding components that differ in at least some respect are further identified in FIGS. 12-22 by a "single prime" designation and are addressed herein.

The body 132' of the power injector coupling 130' has a first end 134 (e.g., a power injector end) and a second end 136' (e.g., a syringe end) that are spaced along the central longitudinal axis 176 of the power injector syringe assembly 170. The second or syringe end 136' of the power injector coupling 130' exists at the coupling flange 142 in the embodiment of FIGS. 12-22. Stated another way, the power injector coupling 130' of FIGS. 12-22 does not include the third cylindrical section 160 that is utilized by the power injector coupling 130 of FIGS. 3-11. As the opening or passageway 140' that extends completely through the power injector coupling 130', or between its first or power injector end 134 and its second or syringe end 136', is thereby different than the opening 140 of the power injector coupling 130 (e.g., based upon the noted lack of a third cylindrical section 160), the opening 140' of the power injector coupling 130' of the embodiment of FIGS. 12-22 is identified by a "single prime" designation. In any case, a ram of a power injector may still extend through this opening 140' to interact (e.g., interface and/or detachably interconnect) with the plunger 122 of the power injector syringe 112 so as to be able to move the plunger 122 relative to the syringe body 113 in at least one direction (e.g., on a discharge stroke, or the plunger 122 is advanced toward the syringe nozzle 118).

The power injector coupling 130' allows the power injector syringe assembly 170 to be installed on a power injector. The cradle 180 provides a receiver of sorts for a power injector syringe 112, and thereby may also be referred to as a power injector syringe receiver 180. Generally, the cradle 180 may be characterized as being on one side of the coupling flange 142 (e.g., a syringe side of the flange 142), while the mounting flange(s) 144 and coupling member(s) 150 of the power injector coupling 130' may be characterized as being on the opposite side of the coupling flange 142 (e.g., a power injector side of the flange 142).

The cradle 180 may be characterized as including a sidewall or base 198 that extends from the coupling flange 142 of the power injector coupling 130' along the central longitudinal axis 176. The cradle 180 (as well as its sidewall 198) may be characterized as an elongated and arcuate structure that extends along the central longitudinal axis 176. In one embodiment, the sidewall 198 of the cradle 180 is defined by a single radius along the entirety of the central longitudinal axis 176 (such a radius being centered on the axis 176). In one embodiment, the cradle 180 extends along the longitudinal axis 176 so as to coincide with at least the barrel 114 of the power injector syringe 112 to be installed therein. That is, in one embodiment the cradle 180 is at least as long as the barrel 114 of the power injector syringe 112 to be installed therein.

The cradle 180 may also include one or more slots 196 that extend completely through the cradle 180 and that may extend along a substantial portion of the cradle 180. The majority of each such slot 196 may be disposed in parallel relation to the longitudinal axis 176. Any appropriate number of slots 196 may be utilized, and any appropriate spacing may be used between each adjacent pair of slots 196. In the illustrated embodiment, there are three slots 196, with each of the two pairs of adjacent slots 196 being equally spaced.

The cradle 180 may be characterized as including a syringe flange receiver section 182, a transition section 184, a syringe barrel section 186, a syringe retention section 188, and an end or end section 190—each of which extends along different portions of the central longitudinal axis 176 (e.g., non-overlapping portions). Notwithstanding this characterization of the cradle 180 including multiple sections, the cradle 180 (along with the entirety of the power injector syringe assembly 170) again may be of an integral or one-piece construction. The syringe flange receiver section 182 extends from the coupling flange 142 of the power injector coupling 130'. The syringe flange 120 of the power injector syringe 112 may be disposed in this syringe flange receiver section 182. The syringe flange receiver section 182 may be defined by the same radius that defines the effective outer diameter of the syringe flange 120. This "effective outer diameter" is the diameter that is defined by a circle that is tangent to the intersection of the various flats that define the perimeter of the syringe flange 120. In the illustrated embodiment, the syringe receiver section 182 is not in the form of a groove or slot that receives the syringe flange 120. That is, the interaction between the syringe flange receiver section 182 and the syringe flange 120 itself does not restrain relative motion between the power injector syringe 112 and the power injector syringe assembly 170 along the central longitudinal axis 176.

The transition section 184 of the cradle 180 extends from the syringe flange receiver section 182 to the syringe barrel section 186 to accommodate the difference between the outer diameter of the syringe barrel section 186 and the effective outer diameter of the syringe flange 120. The transition section 184 may be characterized as being between the syringe flange receiver section 182 and the syringe barrel section 186 relative to the central longitudinal axis 176. The syringe barrel section 186 in turn extends from the transition section 184 to the syringe retention section 188, while the syringe retention section 188 extends from the syringe barrel section 186 to the end section 190. The syringe retention section 188 may be characterized as being between the syringe barrel section 186 and the end section 190 relative to the central longitudinal axis 176. The above-noted slots 196 may extend parallel to the central longitudinal axis 176 over the entire length of the syringe barrel section 184 (and along at least part of the syringe retention section 188 as well).

The end section 190 of the cradle 180 may define the second or syringe nozzle end 174 of the power injector syringe assembly 170. In this regard, the end section 190 includes a syringe nozzle aperture 192 through which the syringe nozzle 118 extends when the syringe 112 is installed in the cradle 180. In one embodiment, the contour/orientation of the end section 190 at least substantially corresponds with the contour/orientation of the transition section 116 of the power injector syringe 112. In one embodiment and at least during a discharge from the power injector syringe 112 (e.g., during operation of a power injector when the power injector syringe assembly 170 is installed thereon), the exterior surface of the transition section 116 of the syringe 112 may be disposed in interfacing relation with the interior surface of the end section 190 of the cradle 180.

A syringe opening 194 may extend along the entire length of the cradle 180 (coinciding with the longitudinal axis 176). However, the width of this syringe opening 194 may vary proceeding along the longitudinal axis 176. The following characterizations regarding the syringe opening 194 may apply individually or in any combination: 1) the syringe retention section 188 may extend more than 180° about the central longitudinal axis 176 to facilitate retention of the syringe 112 during operation of a power injector that utilizes the power injector syringe assembly 170; 2) each of the syringe flange receiver section 182, the transition section 184, and the syringe barrel section 186 may extend no more than 180° about the longitudinal axis 176; and 3) each of the syringe flange receiver section 182, the transition section 184, and the syringe barrel section 186 may extend 180° about the longitudinal axis 176.

The cradle 180 of the power injector syringe assembly 170 receives a corresponding power injector syringe 112. The syringe 112 may be positioned within the power injector syringe assembly 170 prior to being installed on a power injector, but will more typically be inserted into the power injector syringe assembly 170 after the power injector syringe assembly 170 has been installed on a power injector (e.g., the power injector syringe assembly 170 may remain on a power injector while syringes 112 are repeatedly installed and removed from the same power injector syringe assembly 170). In any case, an appropriate power injector syringe 112 may be aligned with the syringe opening 194 of the cradle 180 and with the syringe 112 and cradle 180 being maintained in parallel relation, and then the syringe 112 may be simply "pushed" into the cradle 180 (e.g., to "snap" the syringe 112 into the cradle 80 by moving the syringe 112 in a vertical dimension, if the cradle 180 is considered to be extending in a horizontal dimension). Another option would be to dispose the syringe 112 at an angle relative to the cradle 180 (e.g., to direct the nozzle 118 and/or a forward section of the syringe barrel 114 under the syringe retention section 188 of the cradle 180), and then advance the syringe 112 relative to the cradle 180 in this angled orientation relative to the cradle 180 until the syringe flange 120 clears the power injector coupling 130', at which time the rear portion of the syringe 112 may then be directed down into the cradle 180.

Figure 23:
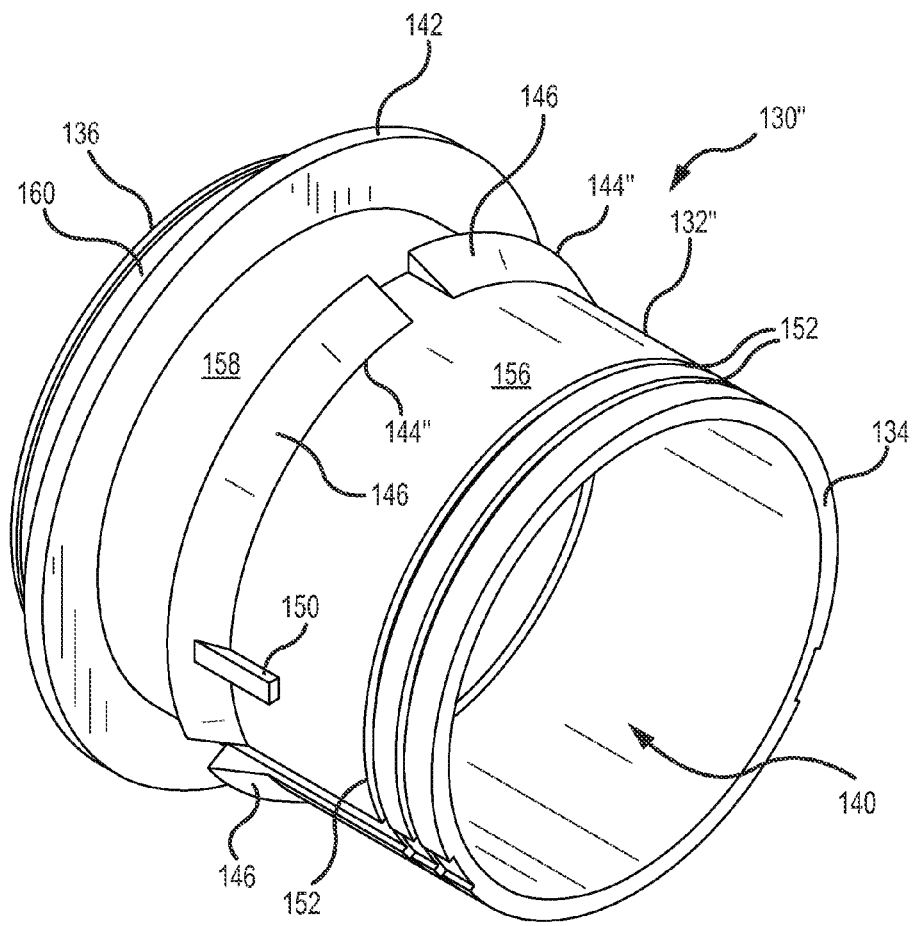
FIG. 23 is a perspective view of a variation of the power injector coupling used by the power injector syringe assembly of FIGS. 3-11.

FIG. 23 presents a variation of the power injector coupling 130 for the power injector syringe assembly 110 (FIGS. 3-11). Instead of using an annular mounting flange 144, the power injector coupling 130" of FIG. 23 uses a plurality of mounting flange segments 144". Each mounting flange segment 144" extends less than 360° about the longitudinal axis 138. Each mounting flange segment 144" may be of any appropriate arcuate extent about the longitudinal axis 138. Multiple mounting flange segments 144" may be disposed about the longitudinal axis 138 and at the same position along the longitudinal axis 138. Any appropriate spacing between each adjacent pair of mounting flange segments 144" may be utilized. In one embodiment, each mounting flange segment 144" is of the same arcuate extent about the longitudinal axis 138, and the mounting flange segments 144" are equally spaced about the longitudinal axis 138.

Figure 24:
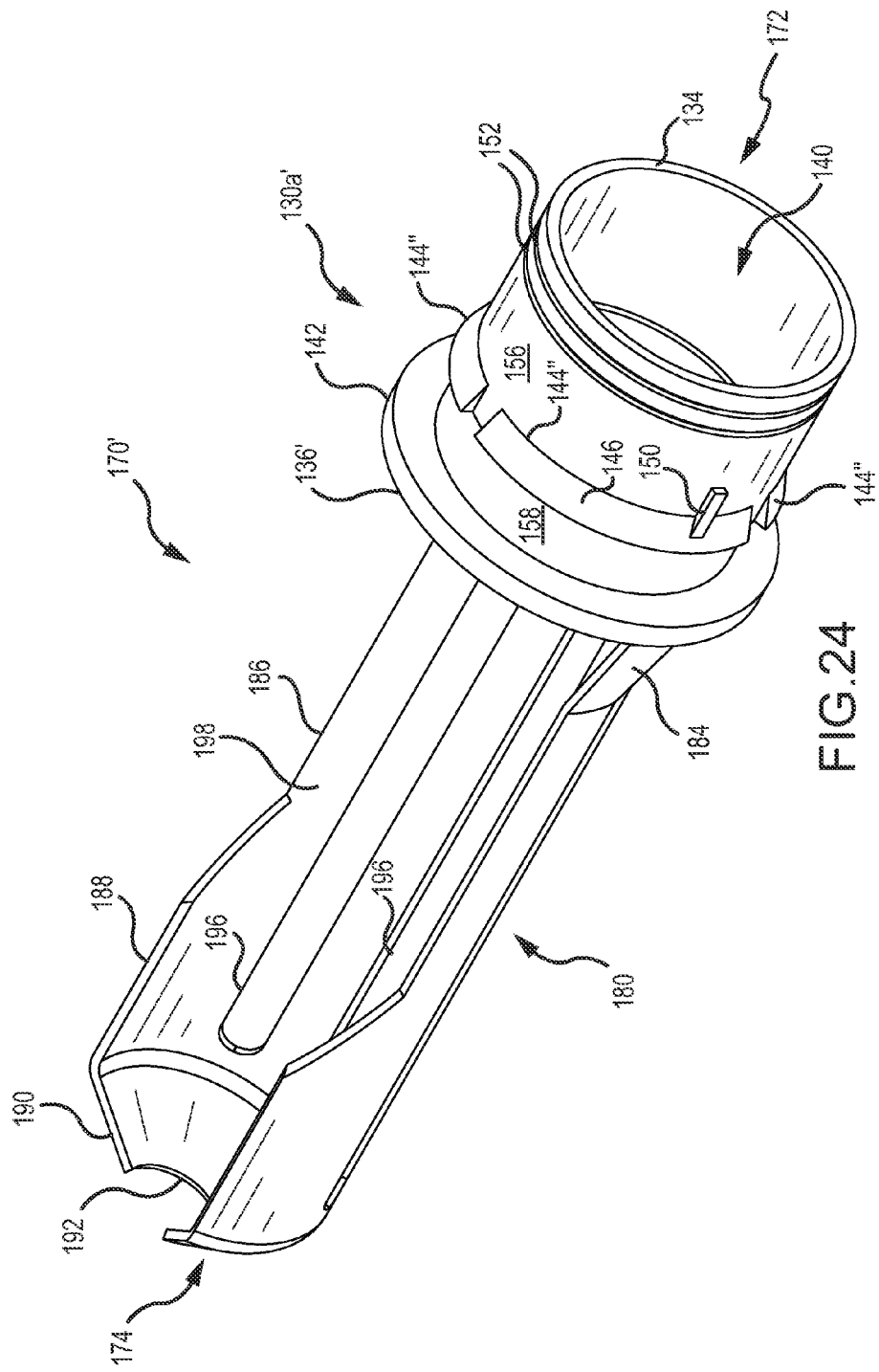
FIG. 24 is a perspective view of a variation of the power injector syringe assembly of FIGS. 12-22.

FIG. 24 presents a variation of the power injector coupling 130' for the power injector syringe assembly 170 (FIGS. 12-22). Instead of using an annular mounting flange 144, the power injector coupling 130a' of FIG. 24 uses a plurality of the mounting flange segments 144" discussed above in relation to FIG. 23.

Figure 25:
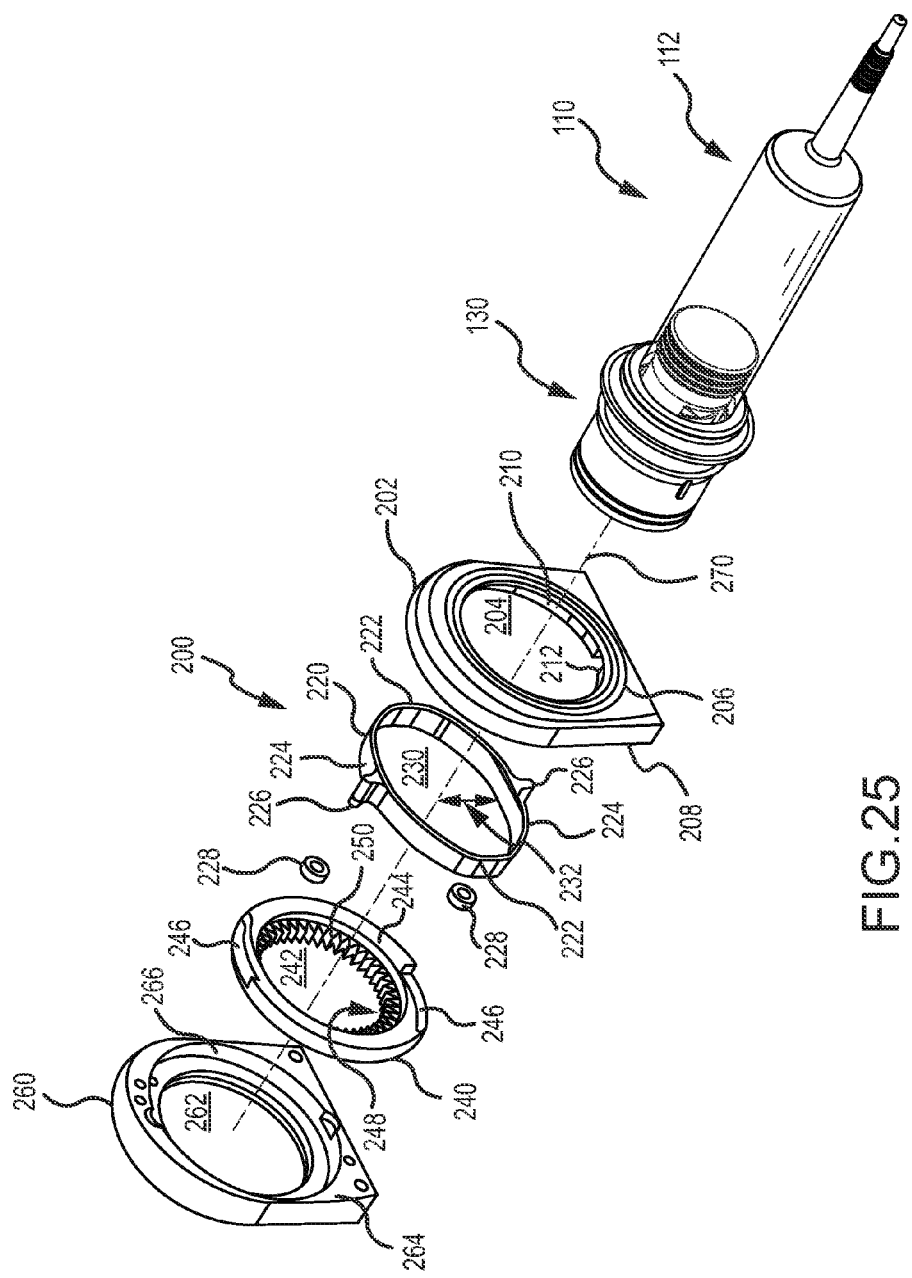
FIG. 25 is an exploded, perspective view (from a front side) of one embodiment of a power injector syringe mount for receiving the power injector syringe assemblies of FIGS. 3-11, 12-22, 23, and 24.
Figure 26:
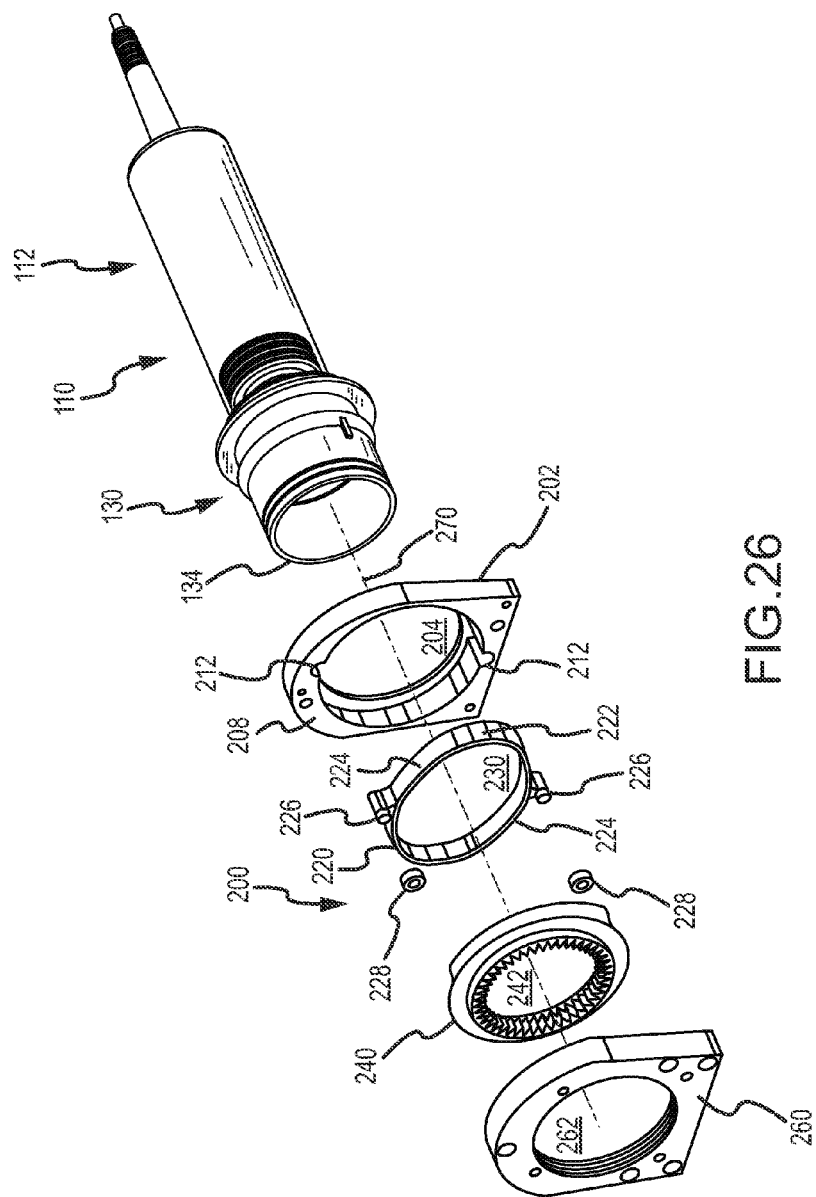
FIG. 26 is an exploded, perspective view (from a back side) of the syringe mount of FIG. 25.

One embodiment of a syringe mount that may be used by a power injector to detachably receive any of the power injector syringe assemblies 110, 170 of FIGS. 3-11 and 12-22 (as well as the variations thereof shown in FIGS. 23 and 24 respectively), respectively, is illustrated in FIGS. 25-26 and is identified by reference numeral 200. The syringe mount 200 includes a housing that is collectively defined by a front plate 202 and a rear plate 260 that may be detachably interconnected in any appropriate manner (e.g., one or more fasteners). Disposed within this housing is a syringe retainer or flex ring 220, along with a syringe retainer actuator or rotating ring 240. Generally, the flex ring 220 may engage the power injector coupling 130/130'/130"/130a' of the power injector syringe assembly 110, 170 to retain the same within the syringe mount 200, while the rotating ring 240 responds to rotation of the power injector syringe assembly 110, 170 to release the flex ring 220 from the power injector coupling 130/130'/130"/130a' to allow the power injector syringe assembly 110, 170 to be removed from the syringe mount 200. Hereafter, the syringe mount 200 will be described in conjunction with the power injector syringe assembly 110, although the discussion is equally applicable to the power injector syringe assembly 170, as well to the cases where the power injector syringe assemblies 110, 170 use the variations shown in FIGS. 23 and 24, respectively.

The front plate 202 includes a hole or passage 204 therethrough. A lip 206 extends around the periphery of the hole 204 through the front plate 202 to abut the power injector syringe coupling 130. The rear surface 208 of the front plate 202 includes an indentation or recess 210 that has essentially the same shape as the flex ring 220. As such, the indentation 210 includes two linear or flattened portions and two curved portions. Two notches 212 in the rear surface 208 of the front plate 202 are positioned at approximately the center point of the curved sections. The notches 212 accommodate a pair of posts 226 of the flex ring 220 and the associated structures that connect the posts 226 to the flex ring 220. The indentation 210 is shaped to be larger than the flex ring 220, and the distance between the notches 212 is greater than the distance between the posts 226 of the flex ring 220 in its relaxed state. The notches 212 help to prevent the flex ring 220 from rotating within the housing of the syringe mount 200, and furthermore permit the flex ring 220 to expand upon rotation of the rotating ring 240 to release the power injector syringe assembly 110 from the syringe mount 200.

The flex ring 220 includes a hole or passage 230 therethrough. A chamfered surface may be provided on a front end of the flex ring 220. Such a chamfered surface may facilitate the insertion of the first or power injector end 134 and mounting flange 144 of the power injector coupling 130 of the power injector syringe assembly 110 within the syringe mount 200. In any case, the flex ring 220 is a substantially elliptically-shaped member that is disposed behind the front plate 202 of the syringe mount 200. The flex ring 220 includes, on either side, a linear or flattened portion 222 that is integrally connected to two curved portions 224. From approximately the midpoint of the curved portions 224, posts 226 extend toward the rear plate 260. The posts 226 extending rearward from the flex ring 220 may be provided with bearings 228. The bearings 228 may be composite bearings (for example, metal and plastic) having inner and outer races with roller bearings disposed therebetween. Alternatively, the bearings 228 may be plastic elements that surround the posts 226 and rotate with respect thereto. In any case, the bearings 228 engage grooves or cam tracks 246 on the rotating ring 240. When the bearings 238 are not used, the posts 236 themselves could engage the grooves or cam tracks 246 on the rotating ring 240.

The rotating ring 240 includes a hole 242 through its center to allow the power injector coupling 130 of the power injector syringe assembly 110 to be disposed therein/directed therethrough. The rotating ring 240, which is disposed to the rear of the flex ring 220 within the housing collectively defined by the font plate 202 and rear plate 260, includes two grooves or cam tracks 246 on its front surface 244. The cam tracks 246 are shaped such that the outer surface thereof increases in diameter along its arc from a closest point to the center of the rotating ring 240 to a farthest point from the center of the ring 240. A plurality of slots or grooves 250 are provided on an inner wall 248 of the rotating ring 240, and are engageable with the coupling members 150 of the power injector coupling 130 to release the power injector syringe assembly 110 from the syringe mount 200. As such, the slots or grooves 250 may also be characterized as coupling members. Generally, rotating the power injector syringe assembly 110 while coupled to the ring 240 (via a coupling between one or more of the coupling members 150 of the power injector coupling 130 with a corresponding one of the grooves 250 on the rotating ring 240) will rotate the ring 240. This rotation of the ring 240 will force the posts 226 apart (by a movement along the cam tracks 246) to stretch the flex ring 220 in a direction indicated by arrows 232.

The rotating ring 240 is disposed within an indentation or recess 266 formed in a front surface 264 of the rear plate 260. The rotating ring 240 is disposed in this indentation 266 so that ring 240 may freely rotate therein. The rear plate 260 also includes a hole or passage 262 therethrough to allow the power injector coupling 130 of the power injector syringe assembly 110 to be disposed therein/directed therethrough.

The power injector syringe assembly 110 may be detachably received by the above-described syringe mount 200. Installing the power injector syringe assembly 110 entails moving the power injector syringe assembly 110 along an axial path relative to the syringe mount 200 (coinciding with longitudinal axis 270 shown in FIGS. 25 and 26). This relative axial movement initially directs the first or power injector end 134 of the power injector coupling 130 into the housing of the syringe mount 200 that is collectively defined by the front plate 202 and the rear plate 260. More specifically, the first or power injector end 134 may be directed through the hole 204 in the front plate 202. Again, the flex ring 220 sits within the indentation 210 formed in the rear surface 208 of the front plate 202 so that the posts 226 of the flex ring 220 engage the notches 212 of the front plate 202. Therefore, when the sloped surface 146 of the mounting flange 144 of the power injector coupling 130 engages the chamfers on the flex ring 220 and as the power injector syringe assembly 110 continues to be axially advanced relative to the syringe mount 200, the mounting flange 144 pushes open the flex ring 220 in the direction indicated by arrows 232 (e.g., such that the flex ring 220 moves from its relaxed distance/state to its extended distance/state).

After the mounting flange 144 of the power injector coupling 130 clears the rear edge of the flex ring 220, the elastic nature of the flex ring 220 causes the flex ring 220 to resume its relaxed state in the direction opposite to the direction indicated by arrows 232. At this time, the flex ring 220 may exert a compressive force on the engaged portion of the power injector coupling 130 (e.g., the second cylindrical section 158). When the flex ring 220 resumes this relaxed state, the end or retention surface 148 of the mounting flange 144 may also engage the rear edge of the flex ring 220. The power injector coupling 130 (and thereby the power injector syringe assembly 110) is thereby held in place by the flex ring 220 and cannot be axially removed from the syringe mount 200 (e.g., the end surface 148 will act as a stop to an attempted axial movement of the power injector coupling 130 away from the syringe mount 200). When the flex ring 220 resumes its relaxed or contracted state, it may provide an audible "click" to indicate to the operator that the power injector coupling 130 has been installed on an injector that includes the syringe mount 200. At this time, the power injector coupling 130 is also disposed within or extends through the hole 242 in the rotating ring 240 to allow the power injector syringe assembly 110 to be disengaged and then removed from the syringe mount 200.

Removal of the power injector coupling 130 from the syringe mount 200 requires that the power injector coupling 130 (and thereby the entirety of the power injector syringe assembly 110) be rotated (e.g., ¼ turn or an approximate one quarter turn) and about the longitudinal axis 270. In this regard, once the power injector coupling 130 has been engaged by the flex ring 220 (e.g., "behind" the mounting flange 144), the projections 150 of the power injector coupling 130 will be engaged with a corresponding groove 250 on the inner wall 248 of the rotating ring 240. As the power injector coupling 130 is rotated (e.g., about the longitudinal axis 270), for example, approximately one quarter turn in, for example, the counter-clockwise direction, the noted projections 150, which engage grooves 250 on the rotating ring 240, force the ring 240 to also rotate approximately the same amount and in the same direction. Alternately, any suitable range of rotation and/or the opposite rotational direction can be used to facilitate disengagement of the power injector coupling 130 from the syringe mount 200.

Because the posts 226 (or any corresponding bearings 228) of the flex ring 220 engage and ride along the cam tracks 246 on the rotating ring 240, the rotation of the ring 240 will urge the flex ring 220 from its relaxed (or power injector coupling engaged) state to its extended (or power injector coupling disengaged) state. As the posts 226 of the flex ring 220 travel along the cam tracks 246 of the rotating ring 240 from the innermost position to the outermost position, the flex ring 220 is stretched from the relaxed distance/state to the extended distance/state, at which point the rear edge of the flex ring 190 disengages or at least sufficiently clears the mounting flange 144 of the power injector coupling 130. Consequently, the power injector coupling 130 is now in a sufficiently disengaged state relative to the syringe mount 200, such that the power injector coupling 130 (along with the entirety of the power injector syringe assembly 110) may be axially removed from the flex ring 220 and the syringe mount 200 (e.g., by a movement along the longitudinal axis 270).

When the power injector coupling 130 is removed from the syringe mount 200, the spring force of the flex ring 220 urges its posts 226 to travel along the cam tracks 246 of the rotating ring 220 from the outer-most position to the inner-most position, thereby returning the flex ring 220 to its relaxed state for receipt of a new syringe or power injector syringe coupling. In addition, when the power injector coupling 130 is disengaged from the flex ring 220, the operator preferably may hear a second audible "click" to indicate that power injector coupling 130 has been disengaged from the syringe mount 200 (and, accordingly, from the corresponding injector).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A power injector syringe assembly, comprising:
   a power injector syringe comprising a syringe barrel, a syringe flange, and a plunger, wherein said plunger is moveable relative to said syringe barrel and comprises a plunger head disposed within said syringe barrel;
   a separate coupling detachably connectable to a power injector syringe mount, wherein said coupling is of an integral construction and lacks any moving part, wherein said coupling comprises a first end and a second end that are spaced along a longitudinal axis that extends through a hollow interior of said coupling, wherein said power injector syringe extends from said second end of said coupling, wherein said coupling further comprises at least one mounting flange and a first coupling member that are each spaced from each of said first and second ends and that are each on an outer perimeter of said coupling, wherein said at least one mounting flange comprises a perimeter surface that slopes outwardly relative to said longitudinal axis proceeding in a direction of said power injector syringe, and wherein said coupling comprises a syringe flange seat that is located between said first end and said second end within said hollow interior and that extends inwardly toward said longitudinal axis from an interior wall of said coupling; and an annular retention ring disposed at said second end of said coupling, wherein said coupling is mounted to said power injector syringe using said retention ring, wherein said retention ring engages said syringe flange within said hollow interior of said coupling, wherein one end surface of said syringe flange of said power injector syringe is seated against said syringe flange seat within said hollow interior of said coupling, wherein an opposite end surface of said syringe flange is engaged by said retention ring within said hollow interior of said coupling, and wherein said retention ring occupies an entirety of an annular space between said syringe barrel and a corresponding portion of said interior wall of said coupling at said second end.

2. The power injector syringe assembly of claim 1, wherein said coupling is permanently joined to said power injector syringe.

3. The power injector syringe assembly of claim 1, wherein said coupling is disposed on an end of said power injector syringe.

4. The power injector syringe assembly of claim 1, wherein said retention ring comprises a first portion disposed within said coupling and a second portion disposed beyond said second end of said coupling.

5. The power injector syringe assembly of claim 1, wherein said coupling and said retention ring are separately positioned relative to said power injector syringe.

6. The power injector syringe assembly of claim 1, wherein said coupling, said retention ring, and said power injector syringe are permanently joined.

7. The power injector syringe assembly of claim 1, wherein said retention ring is disposed about said syringe barrel within said hollow interior of said coupling.

8. The power injector syringe assembly of claim 1, wherein said coupling comprises a coupling flange, wherein said at least one mounting flange is spaced from said coupling flange.

9. The power injector syringe assembly of claim 8, wherein said coupling flange is annular.

10. The power injector syringe assembly of claim 8, wherein said coupling flange comprises a fixed outer diameter.

11. The power injector syringe assembly of claim 8, wherein a perimeter of said coupling flange defines a maximum outer diameter of said coupling.

12. The power injector syringe assembly of claim 8, wherein said coupling flange is of an integral construction.

13. The power injector syringe assembly of claim 8, wherein a maximum thickness of said coupling flange is within a range of about 0.010" to about 0.020".

14. The power injector syringe assembly of claim 8, wherein said coupling further comprises first and second cylindrical sections disposed on opposite sides of said coupling flange.

15. The power injector syringe assembly of claim 14, wherein said first and second cylindrical sections extend from said coupling flange in opposite directions, wherein said first cylindrical section is on a power injector side of said coupling flange, and wherein said second cylindrical section is on a power injector syringe side of said coupling flange.

16. The power injector syringe assembly of claim 15, wherein said first and second cylindrical sections have different outer diameters.

17. The power injector syringe assembly of claim 15, wherein said first cylindrical section extends from said coupling flange to said at least one mounting flange.

18. The power injector syringe assembly of claim 17, wherein an outer diameter of said at least one mounting flange increases proceeding in the direction of said coupling flange.

19. The power injector syringe assembly of claim 1, wherein said at least one mounting flange comprises a wedge-shaped cross-section.

20. The power injector syringe assembly of claim 1, wherein an outer diameter of said at least one mounting flange increases proceeding in a direction away from said first end.

21. The power injector syringe assembly of claim 1, wherein said at least one mounting flange comprises a cam.

22. A power injector, comprising:
the power injector syringe assembly of claim 1;
a syringe plunger driver comprising a motorized drive source; and
a syringe mount comprising a syringe retainer and an syringe retainer actuator, wherein said syringe retainer actuator interacts with said syringe retainer and comprises a second coupling member, wherein said at least one mounting flange engages and expands said syringe retainer during installation of said power injector syringe assembly to said syringe mount, wherein said first and second coupling members are engageable, and wherein rotation of said power injector syringe assembly while said first and second coupling members are engaged expands said syringe retainer to allow said power injector syringe assembly to be removed from said syringe mount.

23. The power injector of claim 22, wherein said syringe retainer actuator comprises a rotatable ring, that in turn comprises a first camming member.

24. The power injector of claim 23, wherein said second coupling member comprises a plurality of grooves disposed about an inner wall of said rotatable ring, and wherein said first coupling member comprises at least one projection on said outer perimeter of said coupling.

25. The power injector of claim 22, wherein said power injector syringe assembly is moved along an axis coinciding with said syringe plunger driver to install said power injector syringe assembly to said syringe mount.

* * * * *